United States Patent [19]

Shutske et al.

[11] Patent Number: 4,695,573
[45] Date of Patent: * Sep. 22, 1987

[54] 9-AMINO-1,2,3,4-TETRAHYDROACRIDIN-1-OL AND RELATED COMPOUNDS

[75] Inventors: Gregory M. Shutske, Somerset, N.J.; Frank A. Pierrat, Coventry, R.I.

[73] Assignee: Hoechst-Roussel Pharmaceuticals Inc., Somerville, N.J.

[ * ] Notice: The portion of the term of this patent subsequent to Mar. 6, 2001 has been disclaimed.

[21] Appl. No.: 781,155

[22] Filed: Oct. 1, 1985

Related U.S. Application Data

[63] Continuation-in-part of Ser. No. 664,730, Oct. 25, 1984, Pat. No. 4,631,286.

[51] Int. Cl.[4] .................... A61K 31/47; C07D 219/10
[52] U.S. Cl. ................... 514/290; 514/297; 514/786; 514/787; 546/79; 546/93; 546/105; 546/106; 558/411; 558/413; 558/423; 558/425
[58] Field of Search ............... 546/79, 93, 105, 106; 514/290, 297

[56] References Cited

U.S. PATENT DOCUMENTS

| | | | |
|---|---|---|---|
| 3,033,866 | 5/1962 | Saggiomo et al. | 546/102 |
| 3,122,553 | 2/1964 | Seneca | 546/105 |
| 3,232,945 | 2/1966 | Sigal, Jr. et al. | 546/105 |
| 3,318,896 | 5/1967 | Pribyl et al. | 546/93 X |
| 4,284,627 | 8/1981 | Raether et al. | 514/297 X |
| 4,550,113 | 10/1985 | Lavretskaya et al. | 514/290 |
| 4,631,286 | 12/1986 | Shutske et al. | 514/297 |

FOREIGN PATENT DOCUMENTS

| | | | |
|---|---|---|---|
| 0179383 | 4/1986 | European Pat. Off. | 514/290 |
| 0532397 | 8/1931 | Fed. Rep. of Germany | 546/79 |

OTHER PUBLICATIONS

Magidson, et al., Chemical Abstracts, vol. 31, 58007 (1937).
Sargent, et al., J. Org. Chem., vol. 11, pp. 350–362 (1946).
Sargent, et al., J. Org. Chem., vol. 12, pp. 567–570, 571–576, (1947).
Sargent, et al., J. Org. Chem., vol. 12, pp. 571–576 (1947).
Stephen, et al., J. Chem. Soc. (1947), pp. 1034–1039.
Desai, et al., J. Indian Chem. Soc., vol. 37, No. 9, pp. 553–556 (1960).
Steinberg, et al., J. Med. Chem., vol. 18, No. 11, pp. 1056–1061 (1975).
Brian, et al., Chemical Abstracts, vol. 62, 6459e (1965).
Albert, The Acridines, 2nd ed., St Martins Press, N.Y. (1966), pp. 431–432.
Patnaik, et al., J. Med. Chem., vol. 9, pp. 483–488 (1966).
Konshin, et al., Chemical Abstracts, vol. 76, 34080k (1972).
Konshin, et al., (T') Chemical Abstracts, vol. 81, 120411d (1974).
Koupilova, et al., Chemical Abstracts, vol. 96, 155388p (1982).
Brian, et al., (II) J. Med. Chem., vol. 8, pp. 143–144 (1965).
Konshin et al., Khim Farm Zh, vol. 5, No. 11, pp. 10–12 (1971).
Davies, Drug Development Research, vol. 5, pp. 69–76 (1985).
Johns, et al., Drug Development Research, vol. 5, pp. 77–96 (1985).
Ellman, et al., Biochemical Pharmacology, vol. 7, pp. 88–95 (1961).
Schindler, et al., Drug Development Research, vol. 4, pp. 567–576 (1984).
Bartus, et al., Science, vol. 209, pp. 301–303 (07/11/80).
Broekkamp, et al., Psychopharmacology, vol. 83, pp. 122–125 (1984).
Komiskey, et al., Psychopharmacology, vol. 73, pp. 304–305 (1981).

Primary Examiner—Donald G. Daus
Assistant Examiner—D. Rivers
Attorney, Agent, or Firm—Tatsuya Ikeda

[57] ABSTRACT

There are disclosed compounds having the formula

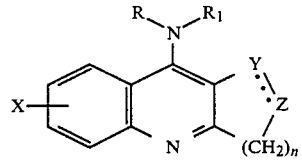

wherein n is 1, 2 or 3; X is hydrogen, loweralkyl, loweralkoxy, halogen, hydroxy, nitro, trifluoromethyl, $NHCOR_2$ where $R_2$ is loweralkyl, or $NR_3R_4$ where $R_3$ and $R_4$ are independently hydrogen or loweralkyl; R is hydrogen or loweralkyl; $R_1$ is hydrogen, loweralkyl, diloweralkylaminoloweralkyl, arylloweralkyl, diarylloweralkyl, furylloweralkyl, thienylloweralkyl, oxygen-bridged arylloweralkyl, oxygen-bridged diarylloweralkyl, oxygen-bridged furylloweralkyl or oxygen-bridged thienylloweralkyl; Y is C=O or $CR_5OH$ where $R_5$ is hydrogen or loweralkyl; Z is $CH_2$ or $C=CR_6R_7$ where $R_6$ and $R_7$ are independently hydrogen or loweralkyl; or Y and Z taken together is $CR_5=CH$ where $CR_5$ and CH correspond to Y and Z respectively; an optical antipode thereof, or a pharmaceutically acceptable acid addition salt thereof, which are useful for enhancing memory, methods for synthesizing them, and pharmaceutical compositions comprising an effective memory enhancing amount of such a compound.

89 Claims, No Drawings

9-AMINO-1,2,3,4-TETRAHYDROACRIDIN-1-OL AND RELATED COMPOUNDS

This is a continuation in part, of application Ser. No. 664,730 filed Oct. 25, 1984, now U.S. Pat. No. 4,631,286.

This invention relates to compounds having the formula

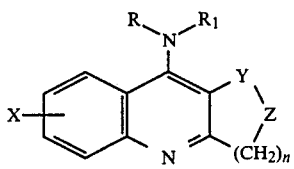

wherein n is 1, 2 or 3; X is hydrogen, loweralkyl, loweralkoxy, halogen, hydroxy, nitro, trifluoromethyl, NHCOR$_2$ where R$_2$ is loweralkyl, or NR$_3$R$_4$ where R$_3$ and R$_4$ are independently hydrogen or loweralkyl; R is hydrogen or loweralkyl; R$_1$ is hydrogen, loweralkyl, diloweralkylaminoloweralkyl, arylloweralkyl, diarylloweralkyl, furylloweralkyl, thienylloweralkyl, oxygen-bridged arylloweralkyl, oxygen-bridged diarylloweralkyl, oxygen-bridged furylloweralkyl or oxygen-bridged thienylloweralkyl; Y is C=O or CR$_5$OH where R$_5$ is hydrogen or loweralkyl; Z is CH$_2$ or C=CR$_6$R$_7$ where R$_6$ and R$_7$ are independently hydrogen or loweralkyl; or Y and Z taken together is CR$_5$=CH where CR$_5$ and CH correspond to Y and Z respectively; an optical antipode thereof, or a pharmaceutically acceptable acid addition salt thereof, which are useful for enhancing memory, methods for synthesizing them, and pharmaceutical compositions comprising an effective memory enhancing amount of such a compound.

This invention also relates to compounds having the formula

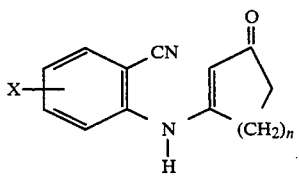

where X and n are as defined above which are useful as intermediate compounds for synthesizing the compounds of Formula I and a method for synthesizing them.

Throughout the specification and the appended claims, a given chemical formula or name shall encompass all stereo and optical isomers thereof where such isomers exist, as well as pharmaceutically acceptable acid addition salts thereof and solvates thereof such as for instance hydrates.

The following definitions shall apply throughout the specification and the appended claims.

Unless otherwise stated or indicated, the term loweralkyl denotes a straight or branched alkyl group having from 1 to 6 carbon atoms. Examples of said loweralkyl include methyl, ethyl, n-propyl, iso-propyl, n-butyl, iso-butyl, sec-butyl, t-butyl and straight- and branched-chain pentyl and hexyl.

Unless otherwise stated or indicated, the term loweralkoxy denotes a straight or branched alkoxy group having from 1 to 6 carbon atoms. Examples of said loweralkoxy include methoxy, ethoxy, n-propoxy, iso-propoxy, n-butoxy, iso-butoxy, sec-butoxy, t-butoxy and straight- and branched-chain pentoxy and hexoxy.

Unless otherwise stated or indicated, the term halogen shall mean fluorine, chorine, bromine or iodine.

Unless otherwise stated or indicated, the term aryl shall mean an unsubstituted phenyl group, a phenyl group substituted with 1, 2 or 3 substituents each of which being independently loweralkyl, loweralkoxy, halogen, hydroxy, trifluoromethyl, phenoxy or benzyloxy, or a phenyl group substituted with four or five fluorine atoms, chlorine atoms or bromine atoms.

Unless otherwise stated or indicated, the term oxygen-bridged shall signify the fact that a non-alpha methylene group present in the loweralkyl group attached to the amino nitrogen which in turn is attached to the fused ring system is replaced by an oxygen atom. Thus, for instance, examples of oxygen-bridged arylloweralkyl include 3-phenoxypropyl and 4-phenoxybutyl, and examples of oxygen-bridged diarylloweralkyl include 2-[bis(4-fluorophenyl)methoxy]ethyl and 2-[bis(3-fluorophenyl)methoxy]ethyl.

The compounds of this invention are prepared by utilizing one or more of the steps described below not necessarily in the order presented.

In order to simplify the description of the synthetic schemes, the description will be presented with specific reference to the situation where n is 2, but it will readily be understood that the synthetic schemes can also be applied to the other situations where n is 1 or 3 by making obvious modifications where necessary.

Throughout the description of the synthetic steps, definitions of X, Y, Z, R and R$_1$ and R$_1$ through R$_7$ are as given above unless otherwise stated or indicated.

STEP A

Compounds of Formula IIa are prepared by reacting a compound of Formula III with 1,3-cyclohexadione. Typically, said reaction is conducted in a suitable solvent such as tetrahydrofuran, diethyl ether, diethylene glycol dimethyl ether, dioxane, benzene or toluene at a temperature of about 30°–120° C.

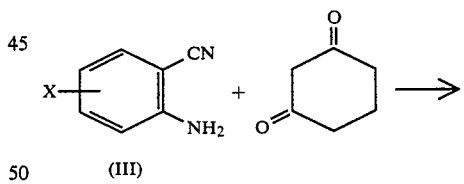

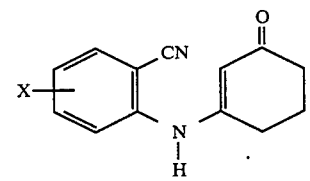

STEP B

Compounds of Formula IV are prepared by cyclizing compound IIa in the presence of a metallic halide such as cuprous chloride, cuprous bromide or cuprous iodide or the like and as a catalyst. Typically said cyclization reaction is conducted in a suitable solvent such as an ethereal solvent including tetrahydrofuran, diethyl ether and dioxane and in the presence of a catalyst and a basic inorganic salt such as potassium carbonate, potassium bicarbonate, sodium carbonate, sodium bicarbonate or the like, at a temperature of about 30°–100° C.

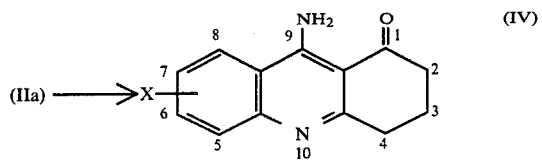

STEP C

Compounds of Formula V (where $R_1$ is not hydrogen and X is not OH, $NHCOR_2$, amino or loweralkylamino) are prepared by reacting compound IV with a compound of the formula $R_1W$, W being Cl, Br, I or $OSO_3CH_3$ (mesyloxy). Typically, said reaction is conducted in a biphasic system comprising a suitable organic solvent such as dichloromethane, chloroform, benzene, toluene or the like, a strongly alkaline aqueous phase such as 50% aqueous NaOH or the like, the starting compounds and a phase transfer catalyst such as tetrabutylammonium hydrogen sulfate at a temperature of about 0°–50° C.

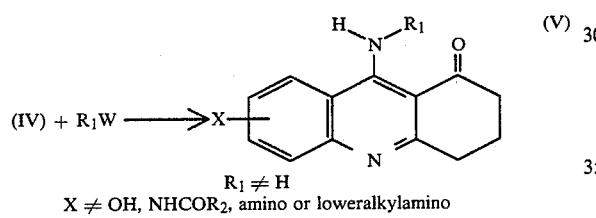

Where X is OH, the excluded compounds can be prepared by subjecting a compound of Formula V where X is a loweralkoxy group (e.g. methoxy group) to a cleavage reaction conducted, for instance, with the aid of pyridine hydrochloride at a temperature of around 180° C.

Where X is amino, the excluded compounds can be prepared from compound V where X is nitro by hydrogenating it in the manner described below as STEP F.

Where X is $NHCOR_2$, the excluded compounds can be obtained by subjecting the corresponding amino compounds ($X=NH_2$) obtained above to an acylation reaction using, for instance, $(R_2CO)_2O$ in substantially the same manner as described below as STEP G.

Where X is loweralkylamino, the excluded compounds can be prepared by reacting the corresponding acylamino compounds ($X=NHCOR_2$) obtained above with a loweralkyl iodide or bromide of the formula $R_3I$ or $R_3Br$ where $R_3$ is loweralkyl in the presence of an inorganic base such as KOH or the like, and hydrolyzing the resultant product where X is

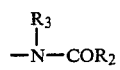

in a routine manner.

STEP D

In a manner similar to the one described above as STEP C, compounds of Formula VI (where neither of $R_1$ and R is hydrogen and X is not OH, $NHCOR_2$, amino or loweralkylamino) are obtained by further reacting compound V with a compound RW, W being the same as defined above.

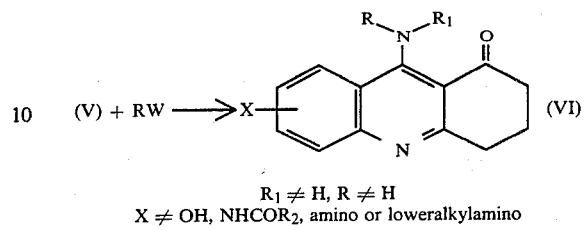

Where X is OH, $NHCOR_2$, amino or loweralkylamino, the excluded compounds can be obtained by use of the reaction schemes described above in STEP C for preparing compounds V where X is OH, $NHCOR_2$, amino or loweralkylamino, respectively.

STEP E

Compounds of Formula VII where $R_1$ is hydrogen or loweralkyl may be prepared by the nitration of a compound of Formula VIII. Said nitration occurs with a good selectivity at the 7-position of the ring. Said reaction is typically conducted in the presence of concentrated sulfuric acid and nitric acid at a temperature of from about −10° to about 30° C.

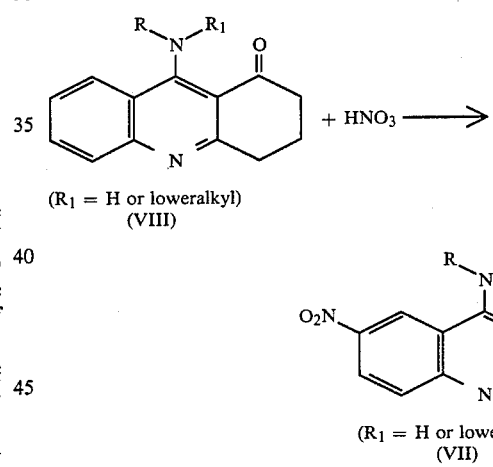

STEP F

Compounds of Formula IX are prepared by the hydrogenation of compound VII in the presence of hydrogen gas and a suitable catalyst such as for instance a noble metal including palladium, platinum, rhodium and the like. Typically, said hydrogenation is conducted in a suitable medium such as glacial acetic acid, ethanol or the like under a suitable hydrogen gas pressure such as about 10–60 psig (pounds per square inch, gauge) at a temperature of about 20°–40° C.

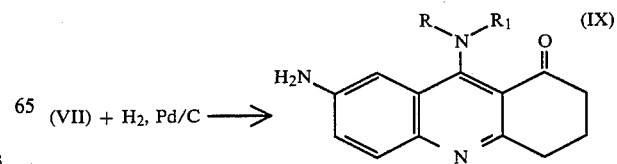

STEP G

Compounds of Formula X are prepared by reacting compound IX with a suitable acylating agent such as an acid anhydride of the formula (R₂CO)₂O or the like in a suitable solvent such as a carboxylic acid of the formula R₂COOH. Typically said reaction is conducted at a temperature of about 80°–120° C.

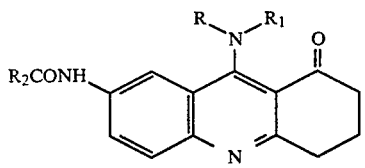

STEP H

Compounds of Formula XI (where X is not NHCOR₂ or NO₂) are prepared by reacting a compound of Formula XII obtained from one of the foregoing STEPS A through G with a suitable metal hydride such as LiAlH₄ in a suitable solvent such as an ethereal solvent including tetrahydrofuran, diethyl ether, dioxane and mixtures thereof at a temperature of from about −20° to about 20° C., and thereafter hydrolyzing the product.

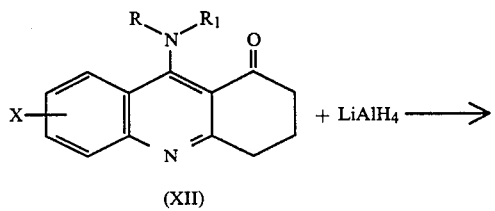

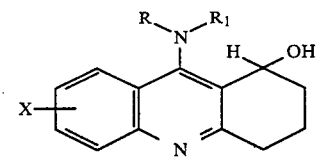

Where X is NO₂, the excluded compounds can be prepared by reducing compounds XII where X is NO₂ with NaBH₄ in a suitable medium such as acetic acid, hydrochloric acid or phosphoric acid aqueous solution.

STEP I

Compounds of Formula XIII (where X is not NHCOR₂) are prepared by reacting compound XII with a suitable organometallic compound such as a compound of the formula R₅Li (where R₅ is loweralkyl) in a suitable solvent such as an ethereal solvent including tetrahydrofuran, diethyl ether and dioxane at a temperature of about 10°–50° C. Subsequent to the reaction of compound XII with R₅Li, the resultant product is hydrolyzed to obtain compound XIII.

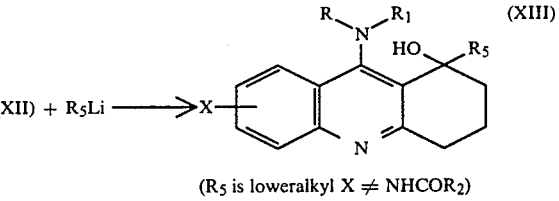

(R₅ is loweralkyl  X ≠ NHCOR₂)

Where X is NHCOR₂ in the above STEPS H or I, the excluded compounds can be prepared in general by use of the above reaction STEPS A through I in a different sequence. For example, compounds of Formula XI-a below can be prepared by use of the sequence depicted below.

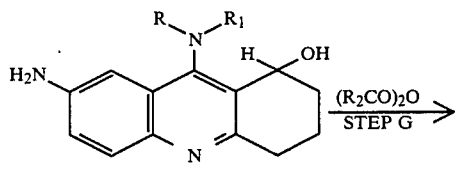

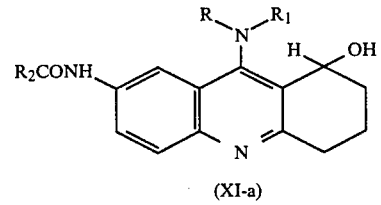

STEP J

Compounds of Formula XIV are prepared by first reacting compound XII with a compound of Formula XV to obtain an intermediate compound of Formula XVI and then converting the latter to compound XIV. The first reaction is conducted typically in a suitable medium such as trifluoroacetic acid, acetic anhydride or an alcohol plus hydrochloric acid at a temperature of about 70°–120° C. The second reaction is conducted typically in a suitable solvent such as toluene, benzene or the like at a temperature of about 80°–120° C.

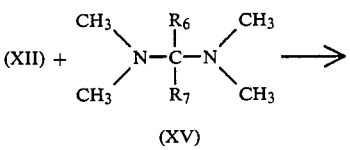

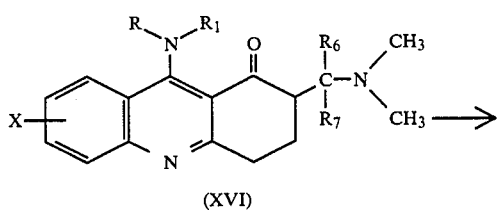

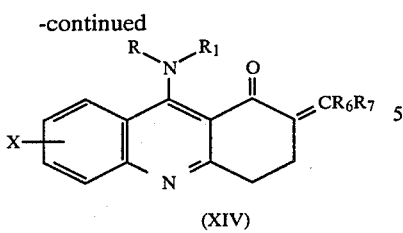

(XIV)

STEP K

Compounds of Formula XVII are prepared by the dehydration rection of compound XI or XIII obtained from STEP H or I above. Typically, said dehydration is conducted in the presence of a suitable solvent such as glacial acetic acid, dimethylformamide, dimethyl sulfoxide or the like and a small amount of acid such as sulfuric acid at a temperature of about 70°–120° C.

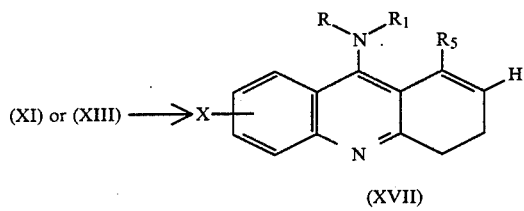

(XVII)

STEP L

Compounds of Formula XVIII (where X is not $NHCOR_2$ or $NO_2$ and $R_5$ is H or loweralkyl) may be prepared by reacting Compound XIV with $(i\text{-}Bu)_2AlH$ or $R_5Li$ ($R_5$ is loweralkyl) in the same manner as described in STEP H or I, respectively.

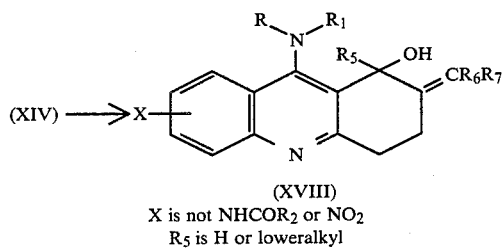

(XVIII)
X is not $NHCOR_2$ or $NO_2$
$R_5$ is H or loweralkyl

Although the foregoing reactions steps are directed to the situation where n is 2, it will be understood that other compounds of this invention where n is 1 or 3 can be prepared by making obvious modifications in the above reaction steps where necessary. Thus, for instance, compounds of formula IIb can be obtained from compound III and 1,3-cyclopentadione in substantially the same manner as STEP A, and compounds of formula XXIX can be obtained by cyclizing said compound IIb in substantially the same manner as STEP B.

(III) + 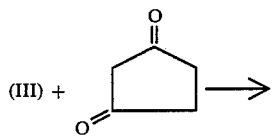 →

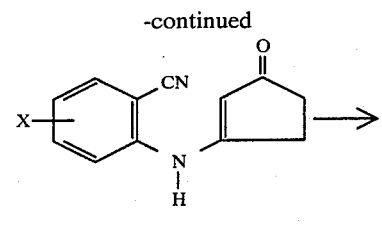

(IIb)

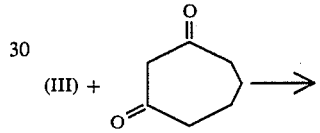

(XXIX)

Similarly, compounds of formula IIc can be obtained from compound III and 1,3-cycloheptadione in substantially the same manner as STEP A, and compounds of formula XXX can be obtained by cyclizing said compound IIc in substantially the same manner as STEP B.

(III) + 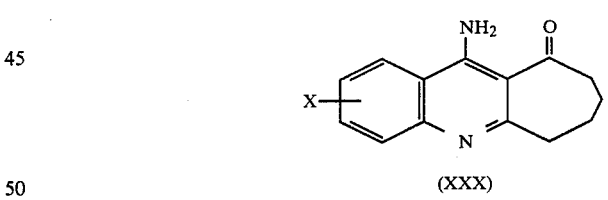

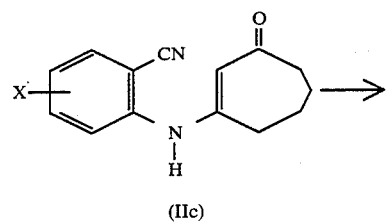

(IIc)

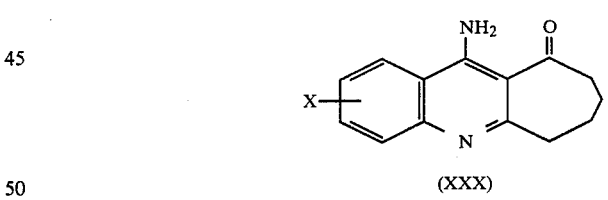

(XXX)

The compounds of formula (I) of the present invention are useful in the treatment of various memory dysfunctions characterized by decreased cholinergic function, such as Alzheimer's disease.

This utility is manifested by the ability of these compounds to inhibit the enzyme cholinesterase and thereby increase acetylcholine levels in the brain.

Additionally, some of the compounds of this invention exhibit antidepressant activities, which activities being particularly helpful for patients suffering from Alzheimer's disease. Further, the compounds of this invention are in general less toxic nd have a broader therapeutic window than heretofore known compounds such as tacrine and physostigmine, making them more therapeutically acceptable.

Cholinesterase Inhibition Assay

The ability to inhibit acetylcholinesterase as determined by the photometric method of Ellman et al., Biochem. Pharmacol. 7, 88 (1961).

| Compound | Cholinesterase Inhibition IC$_{50}$(molar) |
| --- | --- |
| 9-Amino-3,4-dihydroacridin-1(2H)—one | $2.5 \times 10^{-4}$ |
| 3,4-Dihydro-9-(4,4-diphenylbutyl)-aminoacridin-1(2H)—one | $1.3 \times 10^{-5}$ |
| 9-Amino-1,2,3,4-tetrahydroacridin-1-ol | $2.3 \times 10^{-5}$ |
| 9-Phenethylamino-1,2,3,4-tetrahydroacridin-1-ol | $2.4 \times 10^{-4}$ |
| 9-Amino-3,4-dihydroacridine | $6.5 \times 10^{-6}$ |
| 9-(2-Fluorobenzyl)amino-1,2,3,4-tetrahydroacridin-1-ol, maleate | $2.1 \times 10^{-4}$ |
| 9-(4-Fluorobenzyl)amino-1,2,3,4-tetrahydroacridin-1-ol | $1.1 \times 10^{-4}$ |
| 3,4-Dihydro-9-(4,4-diphenylbutyl)-aminoacridin-1(2H)—one | $1.3 \times 10^{-5}$ |
| 1,2,3,4-Tetrahydro-9-(4-trifluoromethylbenzyl)aminoacridin-1-ol | $5.5 \times 10^{-4}$ |
| 1,2,3,4-Tetrahydro-9-(2-trifluoromethylbenzyl)aminoacridin-1-ol | $9.2 \times 10^{-4}$ |
| 9-(2-Chlorobenzyl)amino-1,2,3,4-tetrahydroacridin-1-ol | $1.3 \times 10^{-4}$ |
| 9-[4,4-Bis(3-fluorophenyl)butylamino]-3,4-dihydroacridin-1(2H)—one | $1.9 \times 10^{-6}$ |
| 9-[(2,3,4,5,6-Pentafluorobenzyl)amino]-1,2,3,4-tetrahydroacridin-1-ol, fumarate | $3.5 \times 10^{-4}$ |
| 9-(2-Methoxybenzylamino)-1,2,3,4,-tetrahydroacridin-1-ol | $1.5 \times 10^{-4}$ |
| (prior art compounds) | |
| 9-Amino-1,2,3,4-tetrahydroacridine (tacrine) | $5.7 \times 10^{-6}$ |
| Physostigmine | $9.2 \times 10^{-8}$ |

This utility is further demonstrated by the ability of these compounds to restore cholinergically deficient memory in the Dark Avoidance Assay, where they are in general active over a broader dose range than heretofore known compounds, a distinct therapeutic advantage.

Dark Avoidance Assay

In this assay mice are tested for their ability to remember an unpleasant stimulus for a period of 24 hours. A mouse is placed in a chamber that contains a dark compartment; a strong incandescent light drives it to the dark compartment, where an electric shock is administered through metal plates on the floor. The animal is removed from the testing apparatus and tested again, 24 hours later, for the ability to remember the electric shock.

If scolopamine, an anticholinergic that is known to cause memory impairment, is administered before an animal's initial exposure to the test chamber, the animal re-enters the dark compartment shortly after being placed in the test chamber 24 hours later. This effect of scopolamine is blocked by an active test compound, resulting in a greater interval before re-entry into the dark compartment.

The results for an active compound are expressed as the percent of a group of animals in which the effect of scopolamine is blocked, as manifested by an increased interval between being placed in the test chamber and re-entering the dark compartment.

| Compound | Dose (mg/kg of Body Weight) | % of Animals Greater than Scopolamine |
| --- | --- | --- |
| 9-Amino-1,2,3,4-tetrahydroacridin-1-ol | 0.63 | 33 |
| 9-Benzylamino-1,2,3,4-tetrahydroacridin-1-ol | 1.25 | 27 |
| 9-Amino-3,4-dihydroacridine | 2.50 | 20 |
| 9-(2-Fluorobenzyl)amino-1,2,3,4-tetrahydroacridin-1-ol, maleate | 2.5 | 27 |
| 9-(4-Fluorobenzyl)amino-1,2,3,4-tetrahydroacridin-1-ol | 1.25 | 33 |
| 3,4-Dihydro-9-(4,4-diphenylbutyl)aminoacridin-1(2H)—one | 0.63 | 50 |
| 1,2,3,4-Tetrahydro-9-(4-trifluoromethylbenzyl)-aminoacridin-1-ol | 0.16 | 22 |
| 1,2,3,4-Tetrahydro-9-(2-trifluoromethylbenzyl)-aminoacridin-1-ol | 0.16 | 38 |
| 9-(2-Chlorobenzyl)amino-1,2,3,4-tetrahydroacridin-1-ol | 0.31 | 27 |
| 9-[4,4-Bis(3-fluorophenyl)-butylamino]-3,4-dihydroacridin-1(2H)—one | 5.0 | 40 |
| 9-Amino-1,2,3,4-tetrahydro-6-trifluoromethylacridin-1-ol | 0.63 | 71 |
| 9-[(2,3,4,5,6-Pentafluorobenzyl)amino]-1,2,3,4-tetrahydroacridin-1-ol, fumarate | 5.0 | 20 |
| 9-Benzylamino-3,4-dihydro-6-fluoroacridin-1(2H)—one, maleate | 5.0 | 40 |
| 9-(2-Methoxybenzylamino)-1,2,3,4-tetrahydroacridin-1-ol | 0.21 | 33 |
| (prior art compounds) | | |
| Tacrine | 0.63 | 13 |
| Pilocarpine | 5.0 | 13 |

Effective quantities of the compounds of the invention may be administered to a patient by any of the various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound.

The solutions or suspension may also include the following components: a sterile diluent such as water for injection, aline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in disposable syringes or multiple dose vials made of glass or plastic.

Examples of the compounds of this invention include:
9-Amino-3,4-dihydroacridin-1(2H)-one;
9-Amino-3,4-dihydro-6-methylacridin-1(2H)-one;
9-Amino-3,4-dihydro-6-methoxyacridin-1(2H)-one;
9-Amino-3,4-dihydro-6-fluoroacridin-1(2H)-one;
9-Amino-6-chloro-3,4-dihydroacridin-1(2H)-one;
9-Amino-7-chloro-3,4-dihydroacridin-1(2H)-one;
9-Amino-3,4-dihydro-6-trifluoromethylacridin-1(2H)-one;
9-Amino-3,4-dihydro-7-nitroacridin-1(2H)-one;
7,9-Diamino-3,4-dihydroacridin-1(2H)-one;
N-[9-Amino-3,4-dihydro-1(2H)-oxoacridin-7-yl]acetamide;
3,4-Dihydro-9-methylaminoacridin-1(2H)-one;
3,4-Dihydro-9-methylamino-7-nitroacridin-1(2H)-one;
3,4-Dihydro-9-propylaminoacridin-1(2H)-one;
3,4-Dihydro-9-[2-(dimethylamino)ethyl]aminoacridin-1(2H)-one;
9-Benzylamino-3,4-dihydroacridin-1(2H)-one;
9-Benzylamino-3,4-dihydro-6-methylacridin-1(2H)-one;
9-Benzylamino-3,4-dihydro-6-fluoroacridin-1(2H)-one;
9-Benzylamino-6-chloro-3,4-dihydroacridin-1(2H)-one;
9-Benzylamino-3,4-dihydro-6-trifluoromethylacridin-1(2H)-one;
3,4-Dihydro-9(2-methylbenzylamino)acridin-1(2H)-one;
3,4-Dihydro-9-(3-methylbenzylamino)acridin-1(2H)-one;
3,4-Dihydro-9-(4-methylbenzylamino)acridin-1(2H)-one;
3,4-Dihydro-9-(2-methoxybenzylamino)acridin-1(2H)-one;
3,4-Dihydro-9-(3-methoxybenzylamino)acridin-1(2H)-one;
3,4-Dihydro-9-(4-methoxybenzylamino)acridin-1(2H)-one;
3,4-Dihydro-9-(2-fluorobenzylamino)acridin-1(2H)-one;
3,4-Dihydro-9-(3-fluorobenzylamino)acridin-1(2H)-one;
3,4-Dihydro-9-(4-fluorobenzylamino)acridin-1(2H)-one;
6-Chloro-3,4-dihydro-9-(4-fluorobenzylamino)acridin-1(2H)-one;
9-(2-Chlorobenzylamino)-3,4-dihydroacridin-1(2H)-one;
9-(3-Chlorobenzylamino)-3,4-dihydroacridin-1(2H)-one;
9-(4-Chlorobenzylamino)-3,4-dihydroacridin-1(2H)-one;
3,4-Dihydro-9-[(2,3,4,5,6-pentafluorobenzyl)amino]acridin-1(2H)-one;
3,4-Dihydro-9-(2-trifluoromethylbenzylamino)acridin-1(2H)-one;
3,4-Dihydro-6-fluoro-9-(2-trifluoromethylbenzylamino)acridin-1(2H)-one;
3,4-Dihydro-9-(3-trifluoromethylbenzylamino)acridin-1(2H)-one;
3,4-Dihydro-9-(4-trifluoromethylbenzylamino)acridin-1(2H)-one;
3,4-Dihydro-9-phenethylaminoacridin-1(2H)-one;
3,4-Dihydro-9-(4,4-diphenylbutyl)aminoacridin-1(2H)-one;
3,4-Dihydro-9-(4,4-diphenylbutylamino)-6-trifluoromethylacridin-1(2H)-one;
9-[4,4-Bis(3-fluorophenyl)butylamino]-3,4-dihydroacridin-1(2H)-one;
9-[4,4-bis(4-fluorophenyl)butylamino]-3,4-Dihydroacridin-1(2H)-one;
3,4-Dihydro-9-(3-phenoxypropylamino)acridin-1(2H)-one;
9-[2-[Bis(4-fluorophenyl)methoxy]ethylamino-3,4-dihydroacridin-1(2H)-one;
9-[4-(Benzyloxy)benzylamino]-3,4-dihydroacridin-1(2H)-one;
3,4-Dihydro-9-[(2-thienyl)methylamino]acridin-1(2H)-one;
9-Amino-2,3-dihydro-cyclopenta[b]quinolin-1-one;
9-Amino-1,2,3,4-tetrahydroacridin-1-ol;
9-Amino-6-chloro-1,2,3,4-tetrahydroacridin-1-ol;
9-Amino-7-chloro-1,2,3,4-tetrahydroacridin-1-ol;
9-Amino-6-methoxy-1,2,3,4-tetrahydroacridin-1-ol;
9-Amino-6-fluoro-1,2,3,4-tetrahydroacridin-1-ol;
9-Amino-1,2,3,4-tetrahydro-6-trifluoromethylacridin-1-ol;
9-Methylamino-1,2,3,4-tetrahydroacridin-1-ol;
9-Propylamino-1,2,3,4-tetrahydroacridin-1-ol;

9-[2-(Dimethylamino)ethyl]amino-1,2,3,4-tetrahydroacridin-1-ol;
9-Benzylamino-1,2,3,4-tetrahydroacridin-1-ol;
9-Benzylamino-6-methyl-1,2,3,4-tetrahydroacridin-1-ol;
9-Benzylamino-6-fluoro-1,2,3,4-tetrahydroacridin-1-ol;
9-Benzylamino-6-chloro-1,2,3,4-tetrahydroacridin-1-ol;
9-Benzylamino-1,2,3,4-tetrahydro-6-trifluoromethylacridin-1-ol;
9-(2-Methylbenzylamino)-1,2,3,4-tetrahydroacridin-1-ol;
9-(3-Methylbenzylamino)-1,2,3,4-tetrahydroacridin-1-ol;
9-(4-Methylbenzylamino)-1,2,3,4-tetrahydroacridin-1-ol;
9-(2-Methoxybenzylamino)-1,2,3,4-tetrahydroacridin-1-ol;
9-(3-Methoxybenzylamino)-1,2,3,4-tetrahydroacridin-1ol;
9-(4-Methoxybenzylamino)-1,2,3,4-tetrahydroacridin-1-ol;
9-(2-Fluorobenzylamino)-1,2,3,4-tetrahydroacridin-1-ol;
9-(3-Fluorobenzylamino)1,2,3,4-tetrahydroacridin-1-ol;
9-(4-Fluorobenzylamino)-1,2,3,4-tetrahydroacridin-1-ol;
6-Chloro-9-(4-fluorobenzylamino)-1,2,3,4-tetrahydroacridin-1-ol;
9-(2-Chlorobenzylamino)-1,2,3,4-tetrahydroacridin-1-ol;
9-(3-Chlorobenzylamino)-1,2,3,4-tetrahydroacridin-1-ol;
9-(4-Chlorobenzylamino)-1,2,3,4-tetrahydroacridin-1-ol;
1,2,3,4-Tetrahydro-9-(2-trifluoromethylbenzyl)aminoacridin-1-ol;
6-Fluoro-1,2,3,4-tetrahydro-9-(2-trifluoromethylbenzylamino)acridin-1-ol;
1,2,3,4-Tetrahydro-9-(3-trifluoromethylbenzylamino)acridin-1-ol;
1,2,3,4-Tetrahydro-9-(4-trifluoromethylbenzylamino)acridin-1-ol;
9-[(2,3,4,5,6-Pentafluorobenzyl)amino]-1,2,3,4-tetrahydroacridin-1-ol;
9-Phenethylamino-1,2,3,4-tetrahydroacridin-1-ol;
9-(4,4-Diphenylbutyl)amino-1,2,3,4-tetrahydroacridin-1-ol;
9-[4,4-Bis(3-fluorophenyl)butylamino]-1,2,3,4-tetrahydroacridin-1-ol;
9-[4,4-Bis(4-fluorophenyl)butylamino]-1,2,3,4-tetrahydroacridin-1-ol;
9-(3-Phenoxypropylamino)-1,2,3,4-tetrahydroacridin-1-ol;
9-[[2-[Bis(4-fluorophenyl)methoxy]ethyl]amino]-1,2,3,4-tetrahydroacridin-1-ol;
9-[4-(Benzyloxy)benzylamino]-1,2,3,4-tetrahydroacridin-1-ol;
9-[(2-Thienyl)methylamino]-1,2,3,4-tetrahydroacridin-1ol;
9-Amino-3,4-dihydroacridine;
9-Amino-1-methyl-1,2,3,4-tetrahydroacridin-1-ol;
9-Amino-3,4-dihydro-2-methyleneacridin-1(2H)-one;
9-Amino-1,2,3,4-tetrahydro-cyclopenta[b]quinolin-1-ol;
2-(3-Oxoclohexen-1-yl)aminobenzonitrile; and
4-Chloro-2-(3-oxocyclohexen-1-yl)aminobenzonitrile.

The following examples are given for illustrative purposes and are not to be considered as limiting the invention disclosed herein. All temperatures are given in degrees Celsius.

EXAMPLE 1

2-(3-oxocyclohexen-1-yl)aminobenzonitrile

In 1.5 liters of tetrahydrofuran was added 98.32 g of anthranilonitrile. The mixture was made acidic to litmus with concentrated HCl and with mechanical stirring war warmed to reflux. To the refluxing solution was added dropwise a solution containing 93.3 g (1 eg) of 1,3-cyclohexadione in 700 ml of tetrahydrofuran. After the addition was complete the reaction mixture was refluxed 0.5 hour more, then cooled and filtered to yield 161 g (91%) of product as an HCl salt, melting point 206° C. A portion of the product was first washed with 10% $Na_2CO_3$ (thus converting it to a free base) and then recrystallized from dichloromethane/hexanes to yield a powder, melting point 210° C.

ANALYSIS: Calculated for $C_{13}H_{12}N_2O$: 73.57% C, 5.70% H, 13.20% N. Found: 73.44% C, 5.79% H, 13.20% N.

EXAMPLE 2

4-Chloro-2-(3-oxocyclohexen-1-yl)aminobenzonitrile hydrochloride

In 75 ml of tetrahydrofuran was dissolved 5.00 g of 2-amino-4-chlorobenzonitrile. Into the mechanically stirred solution was bubbled HCl gas until a slurry was formed. The gas was disconnected and the slurry was brought to reflux. To the refluxing slurry was added dropwise over 10 minutes a solution containing 3.67 g (1.1 eq) of 1,3-cyclohexadione in 75 ml of tetrahydrofuran. Reflux was continued for 0.5 hour during which the reaction went to completion. The slurry was cooled and filtered and the filter cake washed with tetrahydrofuran to yield 8.87 g (96%) of a solid, melting point 229° C. (with decomposition).

ANALYSIS: Calculated for $C_{13}H_{11}ClN_2O$ HCl: 55.13% C, 4.27% H, 9.89% N. Found: 55.35% C, 4.55% H, 9.74% N.

EXAMPLE 3

9-Amino-3,4-dihydroacridin-1(2H)-one

In 2 liters of tetrahydrofuran were combined 219.3 g of 2-(3-oxocyclohexen-1-yl)aminobenzonitrile hydrochloride, 250 g (2 eq) of milled $K_2CO_3$, and 3 g of CuCl catalyst. The mechanically stirred mixture was refluxed 5 hours and then filtered hot to remove the inorganic salts. The filtrate was evaporated to a residue and the residue as recrystallized twice from isopropanol to yield 77.4 g (41%) of a powder, melting point 236°–238° C.

ANALYSIS: Calculated for $C_{13}H_{12}N_2O$: 73.57% C, 5.70% H, 13.20% N. Found: 73.37% C, 5.83% H, 13.20% N.

EXAMPLE 4

9-Benzylamino-3,4-dihydroacridin-1(2H)-one

In a biphasic solution consisting of 150 ml of dichloromethane and 100 ml of 50% aqueous NaOH were added 4.00 g of 9-amino-3,4-dihydroacridin-1-(2H)-one, and 0.96 g of tetrabutylammonium hydrogensulfate catalyst. The mixture was stirred mechanically for 0.5 hour and thereafter 2.47 ml (1.1 eq) of benzyl bromide was added in one portion. After 4 hours of vigorous stirring, the reaction appeared complete based on thin layer chromatography analysis. The reaction mixture was poured into water/ice and the dichloromethane layer separated, dried over $MgSO_4$ and evaporated to a solid. The solid was recrystallized three times from dichloromethane/hexanes to yield 2.35 g (41%) of product, melting point 162°–163° C.

ANALYSIS: Calculated for $C_{20}H_{18}N_2O$: 79.44% C, 6.00% H, 9.25% N. Found: 79.43% C, 6.11% H, 9.31% N.

EXAMPLE 5

3,4-Dihydro-9-(methylamino)acridin-1(2H)-one

In 150 ml of dichloromethane and 100 ml of 50% NaOH were added 5.00 g of 9-amino-3,4-dihydroacridin-1(2H)-one and 0.80 g (0.1 eq) of tetrabutylammonium hydrogensulfate. The biphasic mixture was mechanically stirred for 0.5 hour and thereafter 4.4 ml (3 eq) of $CH_3I$ was added. The reaction mixture was stirred overnight. Analysis of the reaction mixture indicated that the starting material was completely consumed. The reaction mixture was poured into cold water and the dichloromethane layer was evaporated, dried over $MgSO_4$ and filtered through alumina and the solvent was evaporated to afford a solid. The solid was recrystallized from dichloromethane/hexanes to yield 3.73 g (70%) of crystalline product after drying, melting point 116°–117° C.

ANALYSIS: Calculated for $C_{14}H_{14}N_2O$: 74.31% C, 6.24% H, 12.38% N. Found: 74.04% C, 6.40% H, 12.37% N.

EXAMPLE 6

9-Amino-1,2,3,4-tetrahydroacridin-1-ol

In 100 ml of dry tetrahydrofuran was added 5.00 g of 9-amino-3,4-dihydroacridin-1(2H)-one. The mechanically stirred suspension was cooled to −5° C. and 21.4 ml (1.0 eq) of 1.1M $LiAlH_4$ solution in ether was added dropwise. After completion of the addition, the reaction mixture was stirred further for 2 hours, whereupon the reaction appeared complete based on thin layer chromatography analysis. The $LiAlH_4$ was neutralized with 2 ml of saturated $NH_4Cl$ and the salts were dissolved with 30% potassium hydroxide. The insoluble product was filtered off and rinsed with water. The precipitate was then dissolved in 3N HCl and the residual insoluble salts filtered off. The acid solution was washed with EtOAc and made basic (pH 9) with 10% NaOH. The precipitated product was filtered and washed with water. After drying at 80° C. under vacuum overnight, 4.15 g (82%) of a powder was obtained, melting point 245° C.

ANALYSIS: Calculated for $C_{13}H_{14}N_2O$: 72.87% C, 6.58% H, 13.07% N. Found: 72.57% C, 6.71% H, 13.00% N.

EXAMPLE 7

3,4-Dihydro-9-(n-propylamino)acridin-1(2H)-one

In a mixture consisting of 150 ml of dichloromethane and 100 ml of 50% NaOH were combined 5.00 g of 9-amino-3,4-dihydroacridin-1(2H)-one and 0.80 g (0.10 eq) of tetrabutylammonium hydrogensulfate. The biphasic mixture was stirred for 0.5 hour and thereafter 6.9 ml (3 eq) of n-propyl iodide was added and the stirring at room temperature was continued for 2 days during which three more portions of the above quantities of the alkylating agent were added at 12 hour intervals. The reaction was then complete based on thin layer chromatography analysis. The organics were separated and purified by passing through an alumina column (dichloromethane). The product was recrystallized from dichloromethane/$Et_2O$ to yield 3.77 g (63%) of a solid, melting point 145° C.

ANALYSIS: Calculated for $C_{16}H_{18}N_2O$: 75.56% C, 7.13% H, 11.01% N. Found: 75.72% C, 7.05% H, 11.02% N.

EXAMPLE 8

9-Amino-3,4-dihydro-7-nitroacridin-1(2H)-one

To 100 ml of cold $H_2SO_4$ was added 5.00 g of 9-amino-3,4-dihydroacridin-1(2H)-one. The mechanically stirred solution was cooled to 0° C. and 2.1 ml (1 eq) of concentrated $HNO_3$ (70 wt % solution) was added dropwise. Stirring was continued for 15 minutes after the addition, whereupon the reaction was complete. The reaction mixture was poured into excess crushed ice and made basic with a slight excess of 50% NaOH solution. More ice was added during the neutralization to keep the solution cool. The resulting precipitate was filtered and chromatographed over silica gel (ETOAc). The fractions containing the product were evaporated to a solid which was triturated with pentane to yield 4.77 g (79%) of a solid after drying, melting point 254° C. (with decomposition).

ANALYSIS: Calculated for $C_{13}N_{11}N_3O_3$: 60.70% C, 4.31% H, 16.33% N. Found: 60.80% C, 4.36% H, 16.38% N.

EXAMPLE 9

9-Methylamino-1,2,3,4-tetrahydroacridin-1-ol

In 50 ml of dry tetrahydrofuran was dissolved 8.00 g of 3,4-dihydro-9-(methylamino)acridin-1(2H)-one. The mechanically stirred solution was cooled to −10° C. under $N_2$ and 32 ml (1 eq) of 1.1M $LiAlH_4$ solution in ether was added over 5 minutes. The stirring was continued for 45 minutes after the addition, during which the reaction went to completion. The excess $LiAlH_4$ was neutralized with 1 ml of saturated $NH_4Cl$ and the resulting salts dissolved in 30% potassium hydroxide solution. The tetrahydrofuran solution was separated and evaporated to an oil which solidified upon trituration with 1:1 dichloromethane/hexanes. The solid was recrystallized from 10:1 hexanes/tetrahydrofuran to yield 5.89 g (73%) of a solid, melting point 160°–161° C.

ANALYSIS: Calculated for $C_{14}H_{16}N_2O$: 73.65% C, 7.06% H, 12.27% N. Found: 73.61% C, 7.00% H, 12.39% N.

EXAMPLE 10

3,4-Dihydro-9-methylamino-7-nitroacridin-1(2H)-one

In 100 ml of concentrated $H_2SO_4$ at 0° C. was added 4.83 g of 3,4-dihydro-9-(methylamino)acridin-1(2H)-one. While maintaining the reaction at 0° C., 1.92 ml (1 eq) of concentrated $HNO_3$ (70 wt %) was added dropwise over 10 minutes. Since the reaction appeared complete after the addition based on thin layer chromatography, the reaction mixture was poured into ice and neutralized with 50% NaOH. At the basic point a precipitate formed. This was filtered and chromatographed on silica gel (EtOAc) and the product was recrystallized from diichloromethane/hexanes to yield 2.75 g (47%) of a solid, melting point 208° C.

ANALYSIS: Calculated for $C_{14}H_{13}N_3O_3$: 61.99% C, 4.83% H, 15.49% N. Found: 61.87% C, 4.79% H, 15.28% N.

EXAMPLE 11

9-(n-Propylamino)-1,2,3,4-tetrahydroacridin-1-ol

In 50 ml of dry tetrahydrofuran was suspended 2.49 g of 3,4-dihydro-9-(n-propylamino)acridin-1(2H)-one. The mechanically stirred suspension was cooled in ice and 4.50 ml (0.5 eq) of 1.1M LiAlH$_4$ solution in ether was added dropwise, whereupon a solution formed. After the addition, the reaction appeared complete based on thin layer chromatography analysis. The excess hydride was neutralized with 0.5 ml of saturated NH$_4$Cl solution and thereafter 30% potassium hydroxide was added to dissolve the salts. The supernatant tetrahydrofuran solution was separated and evaporated to a solid. The solid was recrystallized from 1:4 dichloromethane/EtOAc to yield 1.88 g (75%) of needles, melting point 164° C.

ANALYSIS: Calculated for C$_{16}$H$_{20}$N$_2$O: 74.97% C, 7.86% H, 10.93% N. Found: 75.02% C, 7.86% H, 10.93% N.

EXAMPLE 12

9-Benzylamino-1,2,3,4-tetrahydroacridin-1-ol

In 75 ml of dry tetrahydrofuran was dissolved 3.81 g of 9-benzylamino-3,4-dihydroacridin-1(2H)-one with mechanical stirring. The solution was cooled in ice under N$_2$ and 5.9 ml (0.5 eq) of 1.1M LiAlH$_4$ solution in ether was added dropwise. After 0.5 hour the reaction was complete based on thin layer chromatography analysis. The excess hydride was neutralized with 0.5 ml of saturated NH$_4$Cl solution and the inorganic salts were extracted into 30% potassium hydroxide. The tetrahydrofuran solution was decanted and evaporated to a solid which was recrystallized from 1:10 dichloromethane/EtOAc to yield 2.89 g (75%) of a solid, melting point 159° C.

ANALYSIS: Calculated for C$_{20}$H$_{20}$N$_2$O: 78.92% C, 6.62% H, 9.20% N. Found: 78.77% C, 6.88% H, 9.20% N.

EXAMPLE 13

9-Amino-1-methyl-1,2,3,4-tetrahydroacridin-1-ol

In 100 ml of dry tetrahydrofuran was suspended 5.00 g of 9-amino-3,4-dihydroacridin-1(2H)-one at ice temperature and 78 ml (4 eq) of 1.2M CH$_3$Li solution in ether was added thereto at such a rate as to avoid bubbling. The reaction mixture was stirred overnight as it warmed to ambient temperature. The next day 20 ml more of the CH$_3$Li solution was added to drive the reaction to a completion. After 0.5 hour the reaction was quenched with excess water and 4.97 g of the precipitate was collected and air dried. The product was recrystallized from MeOH/toluene. The yield was 2.06 g (38%) of granules, melting point 250° C.

ANALYSIS: Calculated for C$_{14}$H$_{16}$N$_2$O: 73.65% C, 7.06% H, 12.27% N. Found: 73.43% C, 7.19% H, 12.19% N.

EXAMPLE 14

9-Amino-3,4-dihydro-2-methyleneacridin-1(2H)-one

In 25 ml of trifluoroacetic acid cooled in ice was dissolved 5.00 g of 9-amino-3,4-dihydroacridin-1(2H)-one. To the solution was added dropwise 6.70 ml (2.09 eq) of bisdimethylaminomethane over 5 minutes and thereafter the mixture was maintained at 90°-100° C. for 5 hours during which the starting material was converted to a mixture of intermediate and exo-methylene products. The reaction mixture was poured into ice/NaOH to make it basic and the precipitate was extracted and several portions of 5:1 dichloromethane/MeOH. The combined extracts were evaporated to a residue. The residue was refluxed in toluene for 5 hours during which the intermediate was converted to the end product. The reaction mixture was evaporated to a residue which was purified by chromatography on silica gel (EtOAc) to yield about 2 g of a solid. This was recrystallized from dichloromethane/EtOAc to yield 1.79 g (34%) of product as a solid, melting point 192°-193° C.

ANALYSIS: Calculated for C$_{14}$H$_{12}$N$_2$O: 74.98% C, 5.39% H, 12.49% N. Found: 75.28% C, 5.50% H, 12.59% N.

EXAMPLE 15

3,4-Dihydro-9-(2-fluorobenzylamino)acridin-1(2H)-one

In a mixture consisting of 150 ml of dichloromethane and 100 ml of 50% NaOH were combined 5.00 g of 9-amino-3,4-dihydroacridin-1(2H)-one, 3 ml (1 eq) of 2-fluorobenzylchloride and 1.20 g (0.15 eq) of tetrabutylammonium hydrogen sulfate. The biphasic mixture was mechanically stirred overnight and 3 ml of 2-fluorobenzylchloride was again added. After 4 hours of further stirring, the reaction was complete based on thin layer chromatography. The reaction mixture was partitioned between water and dichloromethane and the dichloromethane layer was separated, dried over MgSO$_4$, filtered and evaporated to a solid. The solid was purified by chromatography on silica gel (ETOAc) and the resultant product was recrystallized from 1:4 EtOAc/toluene to yield 4.09 g (54%) of a solid, melting point 163.5°-164° C.

ANALYSIS: Calculated for C$_{20}$H$_{17}$FN$_2$O: 74.98% C, 5.35% H, 8.74% N. Found: 74.80% C, 5.42% H, 8.76% N.

EXAMPLE 16

7,9-Diamino-3,4-dihydroacridin-1-(2H)-one

In 250 ml of glacial acetic acid was dissolved 4.43 g of 9-amino-3,4-dihydro-7-nitroacridin-1(2H)-one and 0.44 g of 10% Pd/C was added. The mixture was put in a 500 ml hydrogenation vessel (Parr) and was shaken under 55 psig (initial) H$_2$. The uptake of H$_2$ was 3 eq before the reaction was complete. The reaction was poured into ice and made basic with 10% NaOH. The precipitate was filtered and dissolved in MeOH. The insoluble Pd/C catalyst was filtered off and the filtrate was diluted with toluene and concentrated until crystallization occurred. The yield was 2.84 g (73%) of a solid, melting point 310° C.

ANALYSIS: Calculated for C$_{13}$H$_{13}$N$_3$O: 68.70% C, 5.77% H, 18.49% N. Found: 68.48% C, 5.90% H, 18.48% N.

EXAMPLE 17

3,4-Dihydro-9-(phenethylamino)acridin-1(2H)-one

In a mixture consisting of 300 ml of dichloromethane and 200 ml of 50% NaOH were combined 10.00 g of 9-amino-3,4-dihydroacridin-1(2H)-one, 28 ml (6 eq) of 2-phenethyl bromide, and 3 g (0.2 eq) of tetrabutylammonium hydrogensulfate catalyst. The mixture was mechanically stirred for 4 days, during which 28 ml of 2-phenethyl bromide was added at intervals of 12 hours. After 4 days the layers were separated and the dichloromethane layer was evaporated to an oil, which was extracted into 3N HCl and washed with ETOAc. The HCl solution was then made basic with 10% NaOH. The resulting precipitate was extracted into dichloromethane and the dichloromethane layer was evaporated to an oil containing mostly the starting material and the end product. The purification method was chromatography on silica gel with 20% EtOAc/dichloromethane solvent. The product thus obtained was recrystallized from dichloromethane/hexanes to yield 2.52 g (17%) of a solid, melting point 129°–132° C.

ANALYSIS: Calculated for $C_{21}H_{20}N_2O$: 79.72% C, 6.37% H, 8.85% N. Found: 79.78% C, 6.39% H, 8.98% N.

EXAMPLE 18

9-Amino-3,4-dihydroacridine hemihydrate

In 50 ml of HOAc was dissolved 3.00 g of 9-amino-1,2,3,4-tetrahydroacridin-1-ol. To this mechanically stirred solution at room temperature was added 0.75 ml (1 eq) of $H_2SO_4$. The reaction mixture was warmed on a steam bath causing a precipitate to form. After 0.5 hour of heating, the reaction was complete based on thin layer chromatography. The reaction mixture was poured into excess ice/10% NaOH and the precipitate was collected. The precipitate was dissolved in dichloromethane, dried over $MgSO_4$, filtered, and evaporated to a solid which was purified by silica gel chromatography to yield a solid. Two recrystallizations from dichloromethane/hexanes yielded 1.40 g (52%) of a powder, melting point 178°–179° C.

ANALYSIS: Calculated for $C_{13}H_{12}N_2\cdot\frac{1}{2}H_2O$: 76.07% C, 6.38% H, 13.65% N. Found: 76.64% C, 6.36% H, 13.73% N.

EXAMPLE 19

N-[9-amino-3,4-dihydro-1(2H)-oxoacridin-7-yl]acetamide

In 50 ml of glacial acetic acid was dissolved 3.00 g of 7,9-diamino-3,4-dihydroacridin-1(2H)-one. The mechanically stirred solution was cooled to 10° C. and 1.37 ml (1.1 eq) of acetic anhydride was added. The solution was then heated on the steam bath for 0.5 hour during which the reaction went to completion. The reaction mixture was poured into ice and made basic with 10% NaOH. The resulting emulsion was centrifuged and the supernatant decanted off. The solid was washed with water and recrystallized from 1:10 MeOH/toluene to yield 2.25 (63%) of a solid, melting point over 260° C.

ANALYSIS: Calculated for $C^{15}H^{15}N^3O_2$: 66.90% C, 5.61% H, 15.60% N. Found: 66.74% C, 5.81% H, 15.56% N.

EXAMPLE 20

9-Amino-7-chloro-3,4-dihydroacridin-1(2H)-one

In 5 liters of toluene were combined 200 ml of dimethylformamide, 180.71 g of 5-chloro-2-(3-oxocyclohexen-1-yl)aminobenzonitrile hydrochloride prepared in the same manner as the compounds of Examples 1 and 2, 176 g (2 eq) of milled $K_2CO_3$ and 3 g of cuprous chloride (CuCl). After 6 hours of reflux 3 g more of CuCl was added. After 12 hours of reflux 3 g more of CuCl was added. After overnight reflux the reaction mixture was evaporated and the residue extracted with dichloromethane via a Soxhlet extraction apparatus for 12 hours. The dichloromethane solution was evaporated to a solid. The solid was suspended in water and $H_2SO_4$ was added. The resultant salt which precipitated out was filtered and made basic with 10% NaOH. The solid was filtered and recrystallized twice from isopropanol/toluene to yield 6.84 g (4%) of a solid, melting point over 260° C.

ANALYSIS: Calculated for $C_{13}H_{11}ClN_2O$: 63.27% C, 4.49% H, 11.35% N. Found: 63.42% C, 4.50% H, 11.28% N.

EXAMPLE 21

3,4-Dihydro-9-(4,4-diphenylbutylamino)acridin-1(2H)-one

In a mixture consisting of 480 ml of dichloromethane and 320 ml of 50% NaOH were combined 8.00 g of 9-amino-3,4-dihydroacridin-1(2H)-one, 68 g (6 eq) of 1-mesyloxy-4,4-diphenylbutane and 2.56 g (0.20 eq) of tetrabutylammonium hydrogensulfate used as a phase transfer catalyst. The biphasic mixture was jacket cooled to 3° C. and was then mechanically stirred for 3 days. As no further reaction occurred, the reaction mixture was diluted with water and the organic phase was separated. Analysis by thin layer chromatography indicated at 1:1 mixture of the end product and the starting material. The dichloromethane layer was evaporated to a gum. The gum was diluted with dichloromethane and mixed with 1:1 alumina/sand to immobilize it as a solid for Soxhlet extraction. The dichloromethane was evaporated and the solid was put into a Soxhlet extraction thimble and extracted with hexane for 4 hours. Since no further extraction occurred after 4 hours, the hexane solution was evaporated to an oil. The oil was chromatographed over silica gel (EtOAc) and the resultant solid rechromatographed through alumina ($Et_2O$) to yield a solid. The solid was recrystallized from $Et_2O$/hexanes to yield 1.22 g (8%) of product, melting point 86°–88° C.

ANALYSIS: Calculated for $C_{29}H_{28}N_2O$: 82.82% C, 6.71% H, 6.66% N. Found: 82.64% C, 6.72% H, 6.61% N.

EXAMPLE 22

9-(2-Fluorobenzylamino)-1,2,3,4-tetrahydroacridin-1-ol maleate

In 250 ml of dry tetrahydrofuran was dissolved 4.80 g of 3,4-dihydro-9-(2-fluorobenzylamino)acridin-1(2H)-one. The mechanically stirred solution was cooled to 0° C. under $N_2$ and 14 ml (1 eq) of 1.1M $LiAlH_4$ in $Et_2O$ was added over 0.5 hour. After the addition the reaction was complete based on thin layer chromatography and hence it was quenched by adding 2 ml of saturated $NH_4Cl$ solution. The inorganics was filtered off and the tetrahydrofuran solution was evaporated to yield a product. The product was recrystallized from dichloromethane hexanes to yield 3.85 g (78%) of a solid, melting point 140°–142° C. to further purify the product 3.39 g of the product was converted to the maleate salt by combining it with 1.1 eq of maleic acid dissolved in isopropanol. The resulting precipitate was recrystallized from 1:4 MeOH/EtOAc to yield 3.75 g of a solid, melting point 151°–152° C.

ANALYSIS: Calculated for $C_{20}H_{19}FN_2O\cdot C_4H_4O_4$: 65.74% C, 5.29% H, 6.39% N. Found: 66.05% c, 5.48% H, 6.42% N.

EXAMPLE 23

9-Phenethylamino-1,2,3,4-tetrahydroacridin-1-ol maleate

In 75 ml of dry tetrahydrofuran was dissolved 2.45 g of 9-phenethylamino-3,4-dihydroacridin-1-(2H)-one. The solution was cooled in ice and 7.0 ml (1 eq) of 1.1M LiAlH$_4$ in Et$_2$O was added dropwise. After 0.5 hour the reaction was complete. It was neutralized with 0.5 ml saturated NH$_4$Cl solution and the resulting inorganic salts were filtered off. The filtrate was evaporated to a solid and the meleate salt was formed by adding a solution of 1.1 eq maleic acid in isopropanol to a suspension of the product in isopropanol. A solution formed initially but the salt precipitated out over 0.5 hour at ambient temperatures. The salt was filtered off and recrystallized from 5:1 EtOAc/MeOH and dried at 80° C. in vacuo to yield 1.14 g (32%) of a solid, melting point 169° C.

ANALYSIS: Calculated for C$_{21}$H$_{22}$N$_2$OC$_4$H$_4$O$_4$: 69.11% C, 6.03% H, 6.45% N. Found: 69.03% C, 6.09% H, 6.37% N.

EXAMPLE 24

9-Amino-7-chloro-1,2,3,4-tetrahydroacridin-1-ol maleate

In 50 ml of dry tetrahydrofuran was suspended 4.00 g of 9-amino-7-chloro-3,4-dihydroacridin-1(2H)-one. The mechanically stirred mixture was cooled in ice and 14.73 ml (1 eq) of 1.1M LiAlH$_4$ in either was added dropwise. After 0.5 hour the reaction was complete. It was quenched with saturated NH$_4$Cl solution and the salts were extracted into 30% potassium hydroxide. The biphasic mixture was diluted with hexanes and the product was collected by filtration, then washed with water and dried in vacuum to yield 3.00 g (75%) of a solid, melting point 164° C. (with decomposition). The meleate salt was prepared by adding 1.1 eq of maleic acid in isopropanol to a suspension of 2.94 g of the product in isopropanol. Initially a solution formed but within a few minutes the salt precipitated out. It was filtered and rinsed with Et$_2$O to yield 3.90 g (91%) of a solid. This was recrystallized from 1:1 MeOH/EtOAc to yield 2.79 g (65%) of a solid, melting point 200° C. (wtih decomposition).

ANALYSIS: Calculated for C$_{13}$H$_{13}$ClN$_2$OC$_4$H$_4$O$_4$:55.96% C, 4.70% H, 7.68% N. Found: 56.29% C, 4.98;1 % H, 7.67% N.

EXAMPLE 25

9-Amino-6-chloro-3,4-dihydroacridin-1(2H)-one

In 200 ml of tetrahydrofuran were combined 5.00 g of 4-chloro 2-(3-oxocyclohexen-1-yl)aminobenzonitrile hydrochloride, 4.88 g (2 eq) milled anhydrous K$_2$CO$_3$, and 0.36 g (0.1 eq) of CuBr.(CH$_3$)$_2$S used as a catalyst. The mechanically stirred mixture was refluxed overnight. It was then evaporated to a residue and extracted with several portions of MeOH. The MeOH extract was evaporated with the residue was chromatographed on silica gel and then the purified product was recrystallized from EtOAc to yield 2.07 g (47%) of a solid, melting point 285°-287° C.

ANALYSIS: Calculated for C$_{13}$H$_{11}$ClN$_2$O: 63.27% C, 4.49% H, 11.35% N. Found: 63.48% C, 4.52% H, 11.52% N.

EXAMPLE 26

9-Amino-6-chloro-1,2,3,4-tetrahydroacridin-1-ol maleate

In 60 ml of dry tetrahydrofuran was suspended 2.79 g of 9-amino-6-chloro-3,4-dihydroacridin-1(2H)-one. The mechanically stirred suspension was cooled to 0° C. and 10.3 ml (1 eq) 1.1M LiAlH$_4$ in ether was added slowly over 5 minutes. The mixture became a solution and after 0.5 hour the reaction was complete based on thin layer chromatography analysis. The reaction was quenched with 200 ml of 30% potassium hydroxide solution added slowly. The two layers were separated and the tetrahydrofuran layer was evaporated to a solid. The solid was suspended in water and a minimal amount of 3N HCl was added to dissolve it. The resultant aqueous solution was washed twice with EtOAc and made slightly basic with 10% NaOH. The resultant precipitate was filtered and air dried to yield 2.76 g (98%) of a solid, melting point 235°-236° C. The solid was suspended in 25 ml of isopropanol and a solution of 1.35 g maleic acid in isopropanol was added thereto. A solution was formed first, but after stirring 0.5 hour the salt precipitated. The mixture was then further cooled in ice and filtered to yield 3.70 g of a solid. This was recrystallized from 1:1 EtOAc/MeOH to yield, after drying at 80° C. under vacuum, 2.41 g (58%) of a solid, melting point 190°-191° C. (with decomposition).

ANALYSIS: Calculated for C$_{13}$H$_{13}$ClN$_2$OC$_4$H$_4$O$_4$: 55.98% C, 4.70% H, 7.68% N. Found: 55.95% C, 4.68% H, 7.88% N.

EXAMPLE 27

9-Amino-3,4-dihydro-6-methylacridine-1(2H)-one, maleate

To a suspension of N-(3-oxo-cyclohexen-1-yl)-2-amino-4-methylbenzonitrile (13.4 g) in 300 ml of tetrahydrofuran was added milled potassium carbonate (9.0 g) and cuprous chloride (600 mg). This was stirred at reflux for 5 hours.

To the reaction mixture was then added 100 ml of warm ethanol and the inorganics were filtered off. The filtrate was then concentrated to give 8.7 g of a solid, mp 292°-297° C. decomp. A 2.3 g portion of this material was suspended in 100 ml of isopropanol and a slight excess of solid maleic acid was added. This was stirred for 5 hours, filtered and dried to give 3.0 g of an analytically pure powder, mp 197°-198° C. decomp.

ANALYSIS: Calculated for C$_{14}$H$_{14}$N$_2$O.C$_4$H$_4$O$_4$: 63.15% C, 5.30% H, 8.18% N. Found: 63.13% C, 5.52% H, 8.18% N.

EXAMPLE 28

9-Amino-3,4-dihydro-6-methoxyacridin-1(2H)-one

2-Amino-4-methoxybenzonitrile (7.51 g) was suspended in 75 ml of benzene containing 6.0 g of cyclohexane-1,3-dione and 1.1 g of p-toluenesulfonic acid monohydrate. The reaction mixture was brought to reflux, at which time a homogeneous solution was obtained. After 15 minutes a thick precipitate developed, which was stirred in the refluxing solvent for an additional 15 minutes. At the end of this time thin layer chromatography (TLC, hereafter) showed that the starting material had been consumed, so the precipitate was filtered off, taken up in 2-butanone, and washed with sodium bicarbonate solution. The organic phase was dried and evaporated to a solid, which was triturated with ether to give 10.61 g of the enamine, mp 194°–196° C.

This material was suspended in 250 ml of tetrahydrofuran to which was then added 11.9 g of milled potassium carbonate and 0.85 g of CuCl. The reaction mixture was then refluxed for a total of 48 hours, with additional portions of CuCl (0.50 g at a time) added at 6 hours and at 30 hour. At the end of this time methanol (100 ml) was added to the reaction mixture and reflux was continued for 15 minutes. It was then filtered through diatomaceous earth, evaporated, and purified by flash chromatography (10% methanol-dichloromethane). Obtained in this manner was 5.1 g of product that was suitable to be carried on to the next step. A 1.5 g portion was recrystallized from methanol to give 1.12 g of analytically pure material, mp 244°–246° C.

ANALYSIS: Calculated for $C_{14}H_{14}N_2O_2$: 69.40% C, 5.82% H, 11.57% N. Found: 69.34% C, 5.80% H, 11.53% N.

EXAMPLE 29

9-Amino-3,4-dihydro-6-fluoroacridin-1(2H)-one

To a suspension of N-(3-oxo-cyclohexen-1-yl)-2-amino-4-fluorobenzonitrile (29.8 g) in 500 ml of tetrahydrofuran was added milled potassium carbonate (21.5 g) and cuprous chloride (1.3 g). This was heated at reflux for 1.5 hours. The reaction mixture was then diluted with 150 ml of dichloromethane/methanol (1:1) and this was filtered. The warm solution was added directly to a column of magnesium silicate and eluted (ethanol/dichloromethane) to give 27.5 g of a powder, mp 269°–273° C. decomp. A portion of this was recrystallized from tetrahydrofuran to give analytically pure crystals, mp 266°–269° C.

ANALYSIS: Calculated for $C_{13}H_{11}FN_2O$: 67.81% C, 4.82% H, 12.17% N. Found: 67.93% C, 5.16% H, 12.21% N.

EXAMPLE 30

9-Amino-3,4-dihydro-6-trifluoromethylacridin-1(2H)-one, maleate

To a solution of N-(3-oxo-cyclohexen-1-yl)-2-amino-4-trifluoromethylbenzonitrile (27.2 g) in 650 ml of tetrahydrofuran were added potassium carbonate (26.8 g) and CuCl (1.9 g). This was heated at reflux for two hours. To this was added 150 ml of ethanol, this was heated to reflux and the suspension was filtered warm. The filtrate was concentrated to a solid.

A 3.7 g portion of the free base was recrystallized from methanol to give 2.0 g of a solid, mp 269°–272° C. This was taken up in 100 ml of warm isopropanol and 25 ml of dichloromethane and the solution was acidified with a solution of maleic acid in isopropanol. The solid which crystallized out was collected to give 2.5 g of a solid, mp 209°–210° C. decomp.

ANALYSIS: Calculated for $C_{14}H_{11}F_3N_2O \cdot C_4H_4O_4$: 54.55% C, 3.82% H, 7.07% N. Found: 54.36% C, 3.70% H, 7.01% N.

EXAMPLE 31

9-Amino-2,3-dihydro-cyclopenta[b]quinolin-1-one, maleate

A suspension of N-(3-oxo-cyclopenten-1-yl)-2-aminobenzonitrile (9.7 g), potassium carbonate (7.4 g) and cuprous chloride (495 mg) in 200 ml of diglyme (diethylene glycol dimethyl ether) was heated at 125° C. for 2.5 hours. The suspension was then solubilized with 140 ml of methanol/dichloromethane and passed through a column of magnesium silicate (ethanol/dichloromethane). The fractions were concentrated to diglyme only and thereafter water was added. The resulting solid was filtered and dried to give 3.7 g of powder, mp 286°–190° C. This was recrystallized from isopropanol to give 2.0 g of powder. This was suspended in 100 ml of isopropanol to which was added maleic acid (1.1 equivalent). The resultant solid was filtered and recrystallized from methanol/diethyl ether to give 2.4 g of powder, mp 191°–193° C. d.

ANALYSIS: Calculated for $C_{12}H_{10}N_2O \cdot C_4H_4O_4$: 61.14% C, 4.49% H, 8.91% N. Found: 60.93% C, 4.50% H, 8.88% N.

EXAMPLE 32

3,4-Dihydro-9-[2-(dimethylamino)ethyl]aminoacridin-1(2H)-one

To a suspension of 9-amino-3,4-dihydroacridin-1(2H)-one (10.0 g) in 100 ml of dimethylformamide was added a 50% suspension of sodium hydride in oil (2.9 g). To this was added 2-dimethylaminoethyl chloride (6.5 g). The mixture was heated to 60° C. pot temperature for 2.5 hours, an additional 2.7 g of the chloride was added and this was heated for an additional 1 hour.

The reaction was then quenched with 200 ml of water and the aqueous phase was extracted with ethyl acetate (3X). The combined organics were then dried over anhydrous magnesium sulfate and preadsorbed on silica.

The desired amine was purified via flash chromatography (ethyl acetate, then progressing to 10% methanol/ethyl acetate) to give 2.65 g of a solid, mp 126°–135° C. This was recrystallized from n-butyl acetate to give 1.3 g of an analytically pure solid, mp 140°–143° C.

ANALYSIS: Calculated for $C_{17}H_{21}N_3O$: 72.05% C, 7.47% H, 14.83% N. Found: 72.38% C, 7.65% H, 14.40% N.

EXAMPLE 33

9-Benzylamino-3,4-dihydro-6-methylacridin-1(2H)-one, maleate

To a suspension of 9-amino-3,4-dihydro-6-methylacridin-1(2H)-one (8.0 g) in 75 ml of dimethylsulfoxide was added pulverized potassium hydroxide (6.0 g). This was stirred to solution and benzyl bromide (7.3 g) was added. This was stirred for 1.5 hours at which time 200 ml of water was added to the reaction flask. The precipitate was filtered, rinsed with water, taken up with dichloromethane and dried over anhydrous magnesium sulfate.

The desired amine was purified via flash chromatography (8% isopropanol/toluene to yield 3.3 g of a solid, mp 141°–149° C. A 1.5 g portion of this material was suspended in 80 ml of isopropanol and 621 mg of maleic acid was added. This was stirred for 3 hours, filtered and dried to give 1.65 g of a powder, mp 151°–153° C.

ANALYSIS: Calculated for $C_{21}H_{20}N_2O \cdot C_4H_4O_4$: 69.43% C, 5.59% H, 6.48% N. Found: 69.15% C, 5.61% H, 6.40% N.

EXAMPLE 34

9-Benzylamino-3,4-dihydro-6-fluoroacridin-1(2H)-one, maleate

To a suspension of 9.0 g of 9-amino-3,4-dihydro-6-fluoroacridin-1(2H)-one in 80 ml of dimethylsulfoxide was added pulverized potassium hydroxide (6.1 g). This was stirred to solution and benzyl bromide (8.4 g) was added. After stirring for 1.5 hours, 200 ml of water was added to the reaction flask. The precipitate was filtered, rinsed with water, dissolved in dichloromethane and dried over anhydrous magnesium sulfate. The resulting solid was triturated with ethyl ether to give 8.8 g of a solid, mp 140°–150° C.

A 3.25 g portion was suspended in isopropanol (80 ml) and 1.3 g of maleic acid was added. The suspension was stirred for 3 hours and filtered to give 3.7 g of a solid, mp 185°–186° C. This was recrystallized from 150 ml of methanol/isopropanol (2:1) to give 2.05 g of analytically pure powder, mp 190°–191° C.

ANALYSIS: Calculated for $C_{20}H_{17}NF_2O \cdot C_4H_4O_4$: 66.05% C, 4.85% H, 6.42% N. Found: 66.30% C, 4.80% H, 6.35% N.

EXAMPLE 35

9-Benzylamino-6-chloro-3,4-dichloroacridin-1(2H)-one

In a biphasic solution comprised of 150 ml of toluene and 100 ml of 30% potassium hydroxide were added 3.00 g of 9-amino-6-chloro-3,4-dihydroacridin-1(2H)-one and 0.62 g of tetrabutylammonium hydrogen sulfate. The reaction was mechanically stirred and brought to reflux (b.p. 90° C.) with a steam bath. To the refluxing mixture was added a solution of 3.04 ml of benzyl bromide in 20 ml of toluene over 0.5 hour. Within 1 hour the reaction was complete by TLC. The toluene layer was separated and the aqueous layer was extracted with ethyl acetate. The organics were combined, dried over anhydrous magnesium sulfate, filtered and evaporated to a solid. The solid was recrystallized from dichloromethane/hexane to yield 1.63 g of a solid, mp 141°–143° C.

ANALYSIS: Calculated for $C_{20}H_{17}ClN_2O$: 71.32% C, 5.09% H, 8.32% N. Found: 71.29% C, 5.18% H, 8.06% N.

EXAMPLE 36

9-Benzylamino-3,4-dihydro-6-trifluoromethylacridin-1(2H)-one

To a suspension of 7.0 g of 9-amino-3,4-dihydro-6-trifluoromethylacridin-1(2H)-one in 75 ml of dimethylsulfoxide was added 6 g of pulverized potassium hydroxide. This was stirred for 10 minutes at ambient temperature. At this time was added benzyl bromide (5.2 g). This was stirred for 2 hours at room temperature.

To the reaction was then added 200 ml of water. The aqueous phase was extracted with ethyl acetate (3X) and the combined organics were washed with water and dried (saturated sodium chloride solution, anhydrous magnesium sulfate).

The desired amine was purified via flash chromatography (3% i-PrOH/$C_6H_5CH_3$) to yield 5.4 g of a solid, mp 128°–134° C. A portion of this was recrystallized from isopropyl ether to give an analytically pure solid, mp 136°–138.5° c.

ANALYSIS: Calculated for $C_{21}H_{17}F_3N_2O$: 68.10% C, 4.63% H, 7.56% N. Found: 68.32% C, 4.61% H, 7.55% N.

EXAMPLE 37

3,4-Dihydro-9-(2-methylbenzylamino)acridin-1(2H)-one 9-amino-3,4-dihydroacridin-1(2H)-one (7.63 g) was suspended in 75 ml of dimethylsulfoxide and 5 g of pulverized 85% potassium hydroxide was added. After 45 minutes a homogeneous solution was obtained to which was added 7.0 g of 2-methylbenzyl bromide. The reaction mixture was stirred for 30 minutes and then additional 2.0 g of the benzyl bromide was added. After 60 more minutes 300 ml of water and 30 ml of ether were added to the reaction. The precipitated product was filtered off and washed with additional ether, then flushed over a short magnesium silicate column with ethyl acetate. After evaporating the solvent, the product was again washed with cold ether to give 7.21 g of product.

ANALYSIS: Calculated for $C_{21}H_{20}N_2O$: 79.71% C, 6.36% H, 8.86% N. Found: 80.17% C, 6.47% H, 8.84% N.

EXAMPLE 38

3,4-Dihydro-9-(3-methylbenzylamino)acridin-1(2H)-one 9-amino-3,4-dihydroacridin-1(2H)-one (7.0 g) was suspended in 75 ml of dimethylsulfoxide and 5.0 g of pulverized 85% potassium hydroxide was added. After stirring for 30 minutes 7.0 g of 3-methylbenzyl bromide was added dropwise. After an additional 30 minutes, another 2.0 g of the benzyl bromide was added. A total of 90 minutes after the addition of the potassium hydroxide, 300 ml of water was added to the reaction mixture and the product was extracted into ethyl acetate. Evaporation of the solvent gave a product that was washed with ether and then flushed over a short magnesium silicate column with ethyl acetate. Evaporation of the solvent gave 6.31 g of product. Analytically pure material was obtained by recrystallization from cyclohexane, mp 134°–136° C.

ANALYSIS: Calculated for $C_{21}H_{20}N_2O$: 79.71% C, 6.37% H, 8.86% N. Found: 79.88% C, 6.22% H, 8.61% N.

EXAMPLE 39

3,4-Dihydro-9-(4-methylbenzylamino)acridin-1(2H)-one 9-amino-3,4-dihydroacridin-1(2H)-one (8.0 g) was suspended in 75 ml of dry dimethylsulfoxide and 6 g of pulverized 85% potassium hydroxide was added. After 1 hour a homogeneous solution was obtained. To this was added 7.4 g of 4-methylbenzyl bromide. After stirring for 60 minutes 200 ml of water was added to the reaction mixture and then the granular precipitate was filtered off. It was taken up in dichloromethane, dried and purified by flash chromatography (5% i-PrOH/toluene) to yield 8.4 g of product. Analytically pure material was obtained by recrystallization from benzene-pentane, mp 143°–144° C.

ANALYSIS: Calculated for $C_{21}H_{20}N_2O$: 79.71% C, 6.37% H, 8.86% N. Found: 79.65% C, 6.58% H, 8.76% N.

EXAMPLE 40

3,4-Dihydro-9-(2-methoxybenzylamino)acridin-1(2H)-one hemihydrate

Eight grams of 9-amino-3,4-dihydroacridin-1(2H)-one was suspended in 75 ml of dimethylsulfoxide and 6 g of pulverized 85% potassium hydroxide was added. After 30 minutes 9.0 g of 2-methoxybenzyl bromide was added dropwise and after another 30 minutes an additional 1.5 g of the benzyl bromide was added. A total of 90 minutes after the addition of the potassium hydroxide, 300 ml of water was added to the reaction mixture, and the precipitated product was filtered off, dissolved in dichloromethane and dried. The solvent was evaporated and the residue purified by flash chromatography (10% i-PrOH/toluene) to give 10.9 g of product. Analytically pure material was obtained by recrystallization from benzene-pentane, mp 111°–112° C.

ANALYSIS: Calculated for $C_{21}H_{20}N_2O_2 \cdot 0.5H_2O$: 73.88% C, 6.20% H, 8.21% N. Found: 73.71% C, 6.15% H, 8.13% N.

EXAMPLE 41

3,4-Dihydro-9-(3-methoxybenzylamino)acridin-1(2H)-one

Eight grams of 9-amino-3,4-dihydroacridin-1(2H)-one was suspended in 75 ml of dimethylsulfoxide and powdered 85% potassium hydroxide (6.0 g) was added. After 30 minutes 3-methoxybenzyl bromide (9.0 g) was added dropwise. After an additional 60 minutes 200 ml of water was added to the reaction mixture and the resultant, slightly gummy precipitate was filtered off. It was taken up in dichloromethane, dried, concentrated and purified by flash chromatography (5% isopropanol/toluene) to give 9.0 g of product. Analytically pure material was obtained by recrystallization from dichloromethane/ether, mp 85°–87° C.

ANALYSIS: Calculated for $C_{21}H_{20}N_2O_2$: 75.88% C, 6.06% H, 8.43% N. Found: 75.61% C, 6.18% H, 8.44% N.

EXAMPLE 42

3,4-Dihydro-9-(4-methoxybenzylamino)acridin-1(2H)-one

Eight grams of 9-amino-3,4-dihydroacridin-1(2H)-one was suspended in 75 ml of dry dimethylsulfoxide (DMSO hereafter) and 3 g of pulverized 85% potassium hydroxide was added. After 1 hour a homogeneous solution was obtained. To this solution was added 8.0 g of 4-methoxybenzyl bromide. After stirring for 90 minutes 300 ml of water was added to the reaction mixture and the product was extracted into ethyl acetate (EtOAc hereafter). The organic phase was dried, concentrated, and purified by flash chromatography (5% methanol-dichloromethane) to give 6.1 g of product as a powder. Analytically pure material was obtained by recrystallization from benzene-pentane, mp 115°–117° C.

ANALYSIS: Calculated for $C_{21}H_{20}N_2O_2$: 75.88% C, 6.06% H, 8.43% N. Found: 76.04% C, 6.30% H, 8.42% N.

EXAMPLE 43

3,4-Dihydro-9-(3-fluorobenzylamino)acridin-1(2H)-one

In 300 ml of toluene and 200 ml of 30% potassium hydroxide were combined 8.00 g of 9-amino-3,4-dihydroacridin-1(2H)-one and 1.92 g of tetrabutylammonium hydrogen sulfate catalyst. The mechanically stirred mixture was heated to reflux and a solution of 9.25 ml of 3-fluorobenzyl bromide in 40 ml of toluene was added over 0.5 hour. Then the reaction was further refluxed for 2 hours. The reaction mixture was then poured into 500 ml of ice and the layers were separated. The aqueous layer was extracted with ethyl acetate. The organics were combined and washed with saturated NaCl solution, dried over magnesium sulfate, filtered and evaporated to a solid. The solid was purified by preparative HPLC (ethyl acetate). The product-containing fractions were combined and concentrated to a solid. The solid was recrystallized from 1:1 dichloromethane/pentane to yield 7.15 g of solid, mp 156°–157° C.

ANALYSIS: Calculated for $C_{20}H_{17}FN_2O$: 74.98% C, 5.35% H, 8.74% N. Found: 75.49% C, 5.43% H, 8.73% N.

EXAMPLE 44

3,4-Dihydro-9-(4-fluorobenzylamino)acridin-1(2H)-one

In 300 ml of toluene and 200 ml of 30% potassium hydroxide were added 8.00 g of 9-amino-3,4-dihydroacridin-1(2H)-one and 1.92 g of tetrabutylammonium hydrogen sulfate catalyst. The mechanically stirred biphasic solution was heated to reflux and 9.4 ml of 4-fluorobenzyl bromide in 50 ml of toluene was added dropwise. Reflux was continued for a total of 2 hours. The reaction was poured onto ice and the toluene layer was separated. The aqueous phase was extracted with ethyl acetate. The organics were combined, washed with saturated NaCl solution, dried over anhydrous magnesium sulfate, filtered and evaporated to a solid. The solid was recrystallized from 1:1 ethyl acetate/hexane to yield 5.89 g of product, mp 158°–159° C.

ANALYSIS: Calculated for $C_{20}H_{17}FN_2O$: 74.98% C, 5.35% H, 8.74% N. Found: 75.25% C, 5.29% H, 8.99% N.

EXAMPLE 45

6-Chloro-3,4-dihydro-9-(4-fluorobenzylamino)acridin-1(2H)-one

In 300 ml of toluene and 200 ml of 30% potassium hydroxide were added 9.00 g of 9-amino-6-chloro-3,4-dihydroacridin-1(2H)-one and 3.10 g of tetrabutylammonium hydrogen sulfate catalyst. The mechanically stirred solution was warmed to reflux (90° C.) and 9.54 ml of 4-fluorobenzyl bromide in 50 ml of toluene was added dropwise over 0.5 hours. After refluxing 3 hours the reaction was complete by TLC. It was poured into 500 ml of ice. The aqueous phase was separated and extracted with dichloromethane (DCM hereafter). The organic layers were combined and washed with saturated NaCl solution, dried over anhydrous magnesium sulfate, filtered and evaporated to an oil. The oil was purified by preparative HPLC (1:1 ethyl acetate/hexane) and the product-containing fractions were combined and evaporated to a solid. The solid was recrystallized from 1:1 DCM/pentane to yield 6.10 g of solid, mp 156°–157.5° C.

ANALYSIS: Calculated for $C_{20}H_{16}ClFN_2O$: 67.70% C, 4.55% H, 7.90% N. Found: 67.73% C, 4.41% H, 7.82% N.

EXAMPLE 46

9-(2-Chlorobenzylamino)-3,4-dihydroacridin-1(2H)-one

To a suspension of 9-amino-3,4-dihydroacridin-1(2H)-one (8.0 g) in 75 ml of dimethyl sulfoxide was added pulverized potassium hydroxide (6.2 g). This was stirred for 0.5 hour at ambient temperature. To this solution was added 2-chlorobenzyl bromide (9.4 g). After 1 hour, an additional 1 ml of the bromide was added. This was stirred for an additional hour. At this time, 200 ml of water was added, and the precipitate was filtered and washed with water. The solid was taken up in dichloromethane and dried over anhydrous magnesium sulfate. The compound was purified via flash chromatography to yield 6.75 g of solid, mp 150°–161° C. A portion of this was recrystallized from methanol to give analytically pure needles, mp 162°–165° C.

ANALYSIS: Calculated for $C_{20}H_{17}ClN_2O$: 71.32% C, 5.09% H, 8.32% N. Found: 71.17% C, 5.25% H, 8.24% N.

EXAMPLE 47

9-(3-Chlorobenzylamino)-3,4-dihydroacridin-1(2H)-one

To a suspension of 9-amino-3,4-dihydroacridin-1(2H)-one (8.0 g) in 75 ml of dimethylsulfoxide was added 6 g of pulverized potassium hydroxide. This was stirred at ambient temperature for 45 minutes. To this was then added 3-chlorobenzyl bromide (8.22 g). After 1.5 hours, another 2.5 ml of the benzyl bromide was added. This was stirred for an additional 45 minutes.

At this time 210 ml of water was added to the reaction vessel. This was stirred to a granular precipitate which was filtered and rinsed with water and diethyl ether. The solid was filtered and stirred in ether and again filtered and dried to yield 6.0 g of a solid, mp 137.5°–140° C. A portion of this was recrystallized from toluene/hexane (1:1) to give an analytically pure solid, mp 139°–141° C.

ANALYSIS: Calculated for $C_{20}H_{17}ClN_2O$: 71.32% C, 5.09% H, 8.32% N. Found: 71.18% C, 5.20% H, 8.34% N.

EXAMPLE 48

9-(4-Chlorobenzylamino)-3,4-dihydroacridin-1(2H)-one

To a suspension of 9-amino-3,4-dihydroacridin-1(2H)-one (8.0 g) in 75 ml of dimethyl sulfoxide was added pulverized potassium hydroxide (6.1 g). This was stirred at room temperature for 0.5 hour. To this solution was added 4-chlorobenzyl chloride (7.63 g) dissolved in 10 ml of dimethyl sulfoxide. This solution was stirred for 3.5 hours at room temperature.

To the reaction mixture was then added 200 ml of water. This was stirred for 0.5 hour after which the precipitate was collected, washed with water, taken up in dichloromethane and dried over anhydrous magnesium sulfate. This was concentrated to a solid which was triturated with ethyl ether to give 9.3 g of a solid, mp 162°–164.5° C.

ANALYSIS: Calculated for $C_{20}H_{17}ClN_2O$: 71.32% C, 5.09% H, 8.325 N. Found: 71.38% C, 5.06% H, 8.26% N.

EXAMPLE 49

3,4-Dihydro-9-[(2,3,4,5,6-pentafluorobenzyl)amino]acridin-1(2H)-one

To a suspension of 9-amino-3,4-dihydroacridin-1(2H)-one (7.45 g) in 70 ml of dimethylsulfoxide was added pulverized potassium hydroxide (6 g). To the resulting solution was added pentafluorobenzyl bromide (10.5 g). This was stirred at ambient temperature for 2 hours.

The reaction mixture was then added to 200 ml of water and extracted with ethyl acetate (3X). The combined organics were washed with water and dried over anhydrous magnesium sulfate. This was added directly to a column of magnesium silicate and eluted with ethyl acetate, whereupon a dark oil was obtained.

The desired amine was purified via flash chromatography (ethyl acetate) to obtain 5.8 g of a solid, mp 119°–124° C. A 2.0 g portion of this solid was recrystallized from ethyl acetate/hexane (1:4) to obtain 1.3 g of an analytically pure powder, mp 122°–124° C.

ANALYSIS: Calculated for $C_{20}H_{13}F_5N_2O$: 61.27% C, 3.34% H, 7.14% N. Found: 61.23% C, 3.28% H, 7.12% N.

EXAMPLE 50

3,4-Dihydro-9-(2-trifluoromethylbenzylamino)acridin-1(2H)-one

In 300 ml of toluene and 200 ml of 30% potassium hydroxide were combined 8.00 g of 9-amino-3,4-dihydroacridin-1(2H)-one and 3.20 g of tetrabutylammonium hydrogen sulfate. The biphasic mixture was mechanically stirred and warmed to reflux (90° C.) and 30.0 g of 2-trifluoromethylbenzyl bromide in 50 ml of toluene was added dropwise over 1 hour. After the addition, heating was maintained for 2 hours during which the reaction went to completion. It was poured into 500 ml of ice and the layers were separated. The aqueous phase was extracted with DCM. The organic solutions were combined, washed with saturated brine, dried over anhydrous magnesium sulfate, filtered, and evaporated to an oil which was purified by preparative HPLC (ethyl acetate). The product-containing fractions were evaporated to a solid which was recrystallized from 1:1 ethyl acetate/hexanes to yield 6.49 g of solid, mp 167° C.

ANALYSIS: Calculated for $C_{21}H_{17}F_3N_2O$: 68.10% C, 4.63% H, 7.56% N. Found: 67.85% C, 4.67% H, 7.55% N.

EXAMPLE 51

3,4-Dihydro-6-fluoro-9-(2-trifluoromethylbenzylamino)acridin-1(2H)-one

To a suspension of 7.6 g of 9-amino-3,4-dihydro-6-fluoroacridin-1(2H)-one in 85 ml of dimethylsulfoxide was added pulverized potassium hydroxide (6.0 g). This was stirred to solution and 2-trifluoromethylbenzyl chloride (7.8 g) was added. This was stirred for a total of 2 hours during which time 2 aliquots of 1 ml of the benzyl chloride was added to the reaction.

To the reaction vessel was then added 210 ml of water and the granular precipitate was filtered, washed with water, dissolved in dichloromethane and dried over anhydrous magnesium sulfate. This was concentrated to a solid which was triturated with ether to give 10.3 g of a solid, mp 146°–151° C.

A 4.0 g portion of this was recrystallized from n-butyl acetate (20 ml ) to yield 3.2 g of an analytically pure powder, mp 149°-152° C.

ANALYSIS: Calculated for $C_{21}H_{16}F_4N_2O$: 64.94% C, 4.14% H, 7.21% N. Found: 64.65% C, 4.25% H, 7.39% N.

EXAMPLE 52

3,4-Dihydro-9-(3-trifluoromethylbenzylamino)acridin-1(2H)-one

In 150 ml of toluene and 700 ml of 30% potassium hydroxide were combined 3.00 g of 9-amino-3,4-dihydroacridin-1(2H)-one and 0.72 g of tetrabutylammonium hydrogen sulfate. The reaction was mechanically stirred and heated with a steam bath. To it was added dropwise a solution of 13.5 g 3-trifluoromethylbenzyl bromide in 30 ml of toluene over 1 hour. After the addition, heating was continued 1 hour during which the reaction went to completion. The organic phase was separated, washed with ice-cold saturated NaCl solution, dried over anhydrous magnesium sulfate, filtered and evaporated to an oil. The oil was diluted with 10 ml of ethyl acetate and purified by preparative HPLC (ethyl acetate). The product-containing fractions were evaporated and recrystallized from DCM/hexane to yield 2.20 g of solid, mp 147°-149° C.

ANALYSIS: Calculated for $C_{21}H_{17}F_3N_2O$; 68.10% C, 4.63% H, 7.56% N. Found: 68.23% C, 4.77% H, 7.60% N.

EXAMPLE 53

3,4-Dihydro-9-(4-trifluoromethylbenzylamino)acridin-1(2H)-one

In 300 ml of toluene and 200 ml of 30% potassium hydroxide were combined 8.00 g of 9-amino-3,4-dihydroacridin-1(2H)-one and 3.20 g of tetrabutylammonium hydrogen sulfate catalyst. The mechanically stirred mixture was warmed to reflux and 30.0 g of 4-trifluoromethylbenzyl bromide in 50 ml of toluene was added dropwise over 1 hour. After stirring at reflux for 4 hours the reaction was complete by TLC. It was poured into 50 ml of ice and the aqueous layer was separated and extracted with DCM. The organics were combined, washed with saturated NaCl solution, dried over anhydrous magnesium sulfate and evaporated to an oil. The oil was purified by preparative HPLC (ethyl acetate) and the isolated product was recrystallized from dichloromethane/pentane (1:1) to yield 3.87 g of solid, mp 174°-176° C.

ANALYSIS: Calculated for $C_{21}H_{17}F_3N_2O$: 68.10% C, 4.63% H, 7.56% N. Found: 68.46% C, 4.81% H, 7.39% N.

EXAMPLE 54

3,4-Dihydro-9-(4,4-diphenylbutylamino)-6-trifluoromethylacridin-1(2H)-one, maleate To a solution of 9-amino-3,4-dihydro-6-trifluoromethylacridin-1(2H)-one in 125 ml of dimethylformamide was added potassium tertiarybutoxide (3.6 g). To the resulting solution was added 4,4-diphenylbutylmethane sulfonate (8.4 g). After 3 hours, an additional 0.8 g of the mesylate and 1 g of the butoxide were added. This was stirred for an additional hour and then quenched with 300 ml of water. The aqueous phase was extracted with ethyl acetate (2X) and the combined organics were washed with water and dried (saturated NaCl solution, magnesium sulfate). This was added directly to a column of magnesium silicate and eluted with ethyl acetate to obtain a dark oil.

The desired amine was purified via preparative HPLC (5% ethyl acetate/dichloromethane) to obtain 2.15 g of a solid, mp 130°-133° C. This was dissolved in ethyl ether and acidified with a solution of maleic acid in isopropanol. The precipitate was collected and dried to obtain 2.4 g of a powder, mp 129°-133° C. This was recrystallized from cyclohexane/acetone (3:1) to obtain 2.10 g of solid, mp 139°-142° C. decomp.

ANALYSIS: Calculated for $C_{30}H_{27}F_3N_2O \cdot C_4H_4O_4$: 67.54% C, 5.17% H, 4.63% N. Found: 67.68% C, 5.20% H, 4.56% N.

EXAMPLE 55

3,4-Dihydro-9-[4,4-bis(3-fluorophenyl)butylamino]acridin-1(2H)-one

To a suspension of 8.0 g of 9-amino-3,4-dihydroacridin-1(2H)-one in 125 ml of dimethylformamide was added potassium tert-butoxide (5.5 g). To this was added 4,4-bis(3-fluorophenyl)butyl methane sulfonate (15.15 g). This was stirred at 90° C. for six hours.

The reaction mixture was then poured into 500 ml of water and extracted with ethyl acetate (3X). The organics were washed with water (2X) and dried (saturated NaCl solution, anhydrous magnesium sulfate).

The amine was purified via flash chromatography (8% i-PrOH/toluene) and then passed through a column of magnesium silicate (ethyl acetate) to yield 11.3 g of a solid, mp 78°-85° C. A portion of this was twice recrystallized from cyclohexane to obtain an analytically pure solid, mp 86°-89° C.

ANALYSIS: Calculated for $C_{29}H_{26}F_2N_2O$: 76.29% C, 5.74% H, 6.14% N. Found: 76.65% C, 6.05% H, 6.11% N.

EXAMPLE 56

3,4-Dihydro-9-[4,4-bis(4-fluorophenyl)butylamino]acridin-1(2H)-one, maleate

To a suspension of 8.0 g of 9-amino-3,4-dihydroacridin-1(2H)-one in 150 ml of dimethylformamide were added potassium tert-butoxide (6.4 g) and 4,4-bis(4-fluorophenyl)butyl chloride (14.0 g). This was heated at 85° C. for 5 hours.

The reaction mixture was then quenched into 400 ml of water and the aqueous phase was extracted with ethyl acetate (3X). The combined organics were washed with water and dried (saturated NaCl solution, anhydrous magnesium sulfate).

The desired amino ketone was purified via flash chromatography (7% i-PrOH/toluene) to yield 6.7 g of a powder, mp 128°-132° C.

A 3.0 portion of this was dissolved in 85 ml of isopropanol and acidified with a solution of maleic acid in isopropanol. The solid which crystallized out was collected and dried to give 3.25 g of a powder, mp 162°-165° C. decomp.

ANALYSIS: Calculated for $C_{29}H_{26}F_2N_2O \cdot C_4H_4O_4$: 69.22% C, 5.28% H, 4.89% N. Found: 69.06% C, 5.19% H, 4.85% N.

EXAMPLE 57

9-(3-Phenoxypropylamino)-3,4-dihydroacridin-1(2H)-one

In 600 ml of toluene and 400 ml of 30% potassium hydroxide were combined 10.00 g of 9-amino-3,4-dihydroacridin-1(2H)-one, 39 ml of 3-phenoxypropyl bromide and 3.2 g of tetrabutylammonium hydrogen sulfate catalyst. The biphasic mixture was refluxed (bp 90° C.) with mechanical stirring for 5 hours, during which the reaction went to completion. The organic phase was separated, washed with ice cold saturated NaCl solution, dried over anhyrous magnesium sulfate, filtered and evaporated to an oil. The oil was flash chromatographed (silica, ethyl acetate) and the product-containing fractions were combined and evaporated to an oil. Trituration with ether yielded the product as a solid which was recrystallized from dichloromethane/hexane to yield 4.45 g of product, mp 104°–106° C.

ANALYSIS: Calculated for $C_{22}H_{22}N_2O_2$: 76.28% C, 6.40% H, 8.09% N. Found: 76.10% C, 6.36% H, 8.10% N.

EXAMPLE 58

9-[2-[Bis(4-fluorophenyl)methoxy]ethylamino]-3,4-dihydroacridin-1(2H)-one, maleate To a cooled suspension of sodium hydride (1.15 g) in 20 ml of dimethylformamide was added a solution of 8.5 g of 9-amino-3,4-dihydroacridin-1(2H)-one in 150 ml of dimethylformamide. This was stirred for 10 minutes at room temperature. At this time, 13.5 g of 2-[Bis(4-fluorophenyl)methoxy]ethyl chloride was added. This was heated at 70° C. for 12 hours.

The reaction mixture was then poured to ice-water and extracted with ethyl acetate (3X). The combined organics were washed with water and dried (saturated NaCl solution, anhydrous mangesium sulfate). This was then passed through a short column of magnesium silicate (ethyl acetate) and concentrated to a semi-solid.

The desired amine was purified via flash chromatography (7% isopropanol/toluene) to give 11.6 g of an oil. This was dissolved in ethyl ether and one-half of this solution was taken. The maleate salt was prepared from ether solution to give 4.45 g of a solid, mp 169°–173° C. d. This was recrystallized from isopropanol/methanol (3:1, 200 ml total volume) to give 2.6 g of an analytically pure powder, mp 176°–178° C. d.

ANALYSIS: Calculated for $C_{28}H_{24}F_2N_2O_2.C_4H_4O_4$: 66.89% C, 4.91% H, 4.88% N. Found: 66.88% C, 4.95% H, 4.85% N.

EXAMPLE 59

9-[4-Benzyloxy)benzylamino]-3,4-dihydroacridin-1(2H)-one

To a suspension of 17.7 g of 9-amino-3,4-dihydroacridin-1(2H)-one in 150 ml of dimethylsulfoxide was added pulverized potassium hydroxide (11 g). To the resulting solution was added 4-benzyloxybenzyl chloride (25 g). This was stirred at ambient temperature for 2.5 hours.

To the reaction vessel was then added 400 ml of water. This was stirred until a granular precipitate was formed which was filtered, rinsed with water, taken up in dichloromethane and dried over anhydrous magnesium sulfate. The resulting semi-solid was triturated (ethyl acetate) to a solid which was passed through a column of mangesium silicate (DCM, then ethyl acetate). This gave 23.8 g of a solid, mp 153°–157° C. A portion of this was recrystallized from n-butyl acetate to give an analytically pure solid, mp 156°–159° C.

ANALYSIS: Calculated for $C_{27}H_{24}N_2O_2$: 79.39% C, 5.92% H, 6.86% N. Found: 79.27% C, 6.10% H, 6.70% N.

EXAMPLE 60

3,4-Dihydro-9-[(2-thienyl)methylamino]acridin-1(2H)-one, maleate

To a suspension of 8.0 g of 9-amino-3,4-dihydroacridin-1(2H)-one in 75 ml of dimethylsulfoxide was added pulverized potassium hydroxide. To the resulting solution was added 2-chloromethylthiophene. This was stirred at ambient temperature for 3 hours.

To the reaction mixture was then added 210 ml of water. The resulting precipitate was collected, rinsed with water, dissolved in dichloromethane and dried over anhydrous magnesium sulfate. This was concentrated to a solid which was triturated with ether to give 8.5 g of a solid, mp 127°–133° C.

A 4.0 g portion was recrystallized from cyclohexane to give 2.8 g of a powder, mp 133°–136° C. This was dissolved in isopropanol/methanol (125 ml:25 ml) and acidified with a solution of maleic acid in isopropanol. The resulting crystals were collected and dried to obtain 3.0 g of analytically pure powder, mp 174°–175° C. decomp.

ANALYSIS: Calculated for $C_{18}H_{16}N_2OS.C_4H_4O_4$: 62.25% H, 4.75% H, 6.60% N. Found: 62.02% C, 4.76% H, 6.50% N.

EXAMPLE 61

9-Amino-6-methoxy-1,2,3,4-tetrahydroacridin-1-ol maleate

9-Amino-3,4-dihydro-6-methoxyacridin-1(2H)-one was suspended in 100 ml of tetrahydrofuran (THF hereafter) and then 17 ml of 1M $LiAlH_4$ in THF was added. Ten minutes after the addition, the reaction mixture was still a suspension but TLC showed that the starting material had been consumed. The reaction was quenched by the sequential addition of 0.6 ml of water, 0.6 ml of 15% sodium hydroxide and 1.8 ml of water. The inorganics were filtered off and washed well with hot THF, and the filtered liquid was combined and concentrated, and the residue triturated with ethyl acetate. The maleate salt was formed by suspending this product in about 50 ml of hot i-PrOH and adding a slight excess of maleic acid. This treatment gave a homogeneous solution to which was added ether until crystallization began. After crystallization was complete the maleate salt was filtered off and dried to obtain 4.60 g of solid, mp 179°–180° C.

ANALYSIS: Calculated for $C_{14}H_{16}N_2O_2.C_4H_4O_4$: 59.99% C, 5.59% H, 7.78% N. Found: 60.00% C, 5.62% H, 7.73% N.

EXAMPLE 62

9-Amino-6-fluoro-1,2,3,4-tetrahydroacridin-1-ol

To a cooled suspension of 5.0 g of 9-amino-3,4-dihydro-6-fluoroacridin-1(2H)-one in 85 ml of tetrahydrofuran was added 22 ml of 1M solution of lithium aluminum hydride in tetrahydrofuran. This was stirred for 1 hour and then quenched with 8 ml of saturated ammonium chloride solution. The inorganics were filtered and rinsed with ethyl acetate, and the combined organics were dried over anhydrous magnesium sulfate. This was filtered and concentrated to obtain 5.0 g of a powder, mp 203°–206° C. d. This was recrystallized from tetrahydrofuran/hexane to obtain 3.95 g of an analytically pure powder, mp 207°–209° C. d.

ANALYSIS: Calculated for $C_{13}H_{13}FN_2O$: 67.23% C, 5.64% H, 12.06% N. Found: 67.60% C, 5.92% H, 12.10% N.

EXAMPLE 63
9-Amino-1,2,3,4-tetrahydro-6-trifluoromethylacridin-1-ol

9-Amino-3,4-dihydro-6-trifluoromethylacridin-1(2H)-one (2.4 g) was suspended in 60 ml of tetrahydrofuran. To this cooled solution was added 9 ml of 1 molar solution of lithium aluminum hydride in THF. This was stirred for 30 minutes.

The reaction was quenched with 5 ml of saturated ammonium chloride solution. This was then diluted with ethyl acetate and the inorganics were filtered and rinsed with ethyl acetate. The combined organics were then dried over anhydrous magnesium sulfate and concentrated to obtain 2.4 g of a solid, mp 221°–225° C. decomp. This was combined with 1.4 g from a previous reaction and recrystallized from tetrahydrofuran/hexane (1:1) to obtain 2.1 g of an analytically pure powder, mp 224°–226° C. decomp.

ANALYSIS: Calculated for $C_{14}H_{13}F_3N_2O$: 59.57% C, 4.64% H, 9.93% N. Found: 59.99% C, 4.67% H, 9.95% N.

EXAMPLE 64
9-[2-(Dimethylamino)ethyl]amino-1,2,3,4-tetrahydroacridin-1-ol

To a cooled solution of 4.4 g of 3,4-dihydro-9-[2-(dimethylamino)ethylamino]acridin-1(2H)-one in 80 ml of tetrahydrofuran was added 8 ml of 1 molar solution of lithium aluminum hydride in THF. This was stirred for ½ hour and then quenched with 6 ml of saturated ammonium chloride solution. The inorganics were filtered and rinsed with ethyl acetate. The combined organics were then dried over anhydrous magnesium sulfate and concentrated to give a solid. This was twice recrystallized from acetone/hexane to give 1.4 g of an analytically pure powder, mp 135°–138° C.

ANALYSIS: Calculated for $C_{17}H_{23}N_3O$: 71.54% C, 8.12% H, 14.72% N. Found: 71.65% C, 8.15% H, 14.78% N.

EXAMPLE 65
9-Benzylamino-6-methyl-1,2,3,4-tetrahydroacridin-1-ol

To a cooled suspension of 3.6 g of 9-benzylamino-3,4-dihydro-6-methylacridin-1(2H)-one in 80 ml of tetrahydrofuran was added 6 ml of 1M solution of lithium aluminum hydride in THF. This was stirred for 1 hour, and thereafter quenched with 7 ml of saturated ammonium chloride solution. The inorganics were filtered and rinsed with ethyl acetate and the combined organics were dried over anhydrous magnesium sulfate. The resulting solid was triturated with ethyl ether to obtain 3.15 g of a solid, mp 148°–153° C. This was recrystallized from toluene (70 ml) to obtain 2.5 g of an analytically pure solid, mp 149°–152° C.

ANALYSIS: Calculated for $C_{21}H_{22}N_2O$: 79.21% C, 6.97% H, 8.80% N. Found: 79.58% C, 7.08% H, 8.76% N.

EXAMPLE 66
9-Benzylamino-6-fluoro-1,2,3,4-tetrahydroacridin-1-ol

To a cooled suspension of 4.85 g of 9-benzylamino-3,4-dihydro-6-fluoroacridin-1(2H)-one in 80 ml of tetrahydrofuran was added 7.5 ml of 1 molar solution of lithium aluminum hydride in THF. This was stirred for 1 hour.

The reaction was then quenched with 5 ml of saturated ammonium chloride solution. The inorganics were filtered and rinsed with ethyl acetate. The combined organics were dried over anhydrous magnesium sulfate and concentrated to a solid which was triturated with ethyl ether to obtain 3.3 g of a powder, mp 155°–162° C. This was recrystallized from ethyl acetate/hexane (120 ml) to obtain 2.4 g of an analytically pure solid, mp 164°–166° C.

ANALYSIS: Calculated for $C_{20}H_{19}FN_2O$: 74.51% C, 5.94% H, 8.69% N. Found: 74.39% C, 5.96% H, 8.58% N.

EXAMPLE 67
9-Benzylamino-6-chloro-1,2,3,4-tetrahydroacridin-1-ol

In 100 ml of dry THF was added 2.90 g of 9-benzylamino-6-chloro-3,4-dihydroacridin-1(2H)-one. The mechanically stirred solution was cooled with ice under nitrogen and 4.3 ml of 1M lithium aluminum hydride solution in THF was added dropwise over 10 minutes. After 1 hour of stirring at 10° C., the reaction was complete by TLC, so it was quenched with 1 ml of saturated ammonium chloride solution. The inorganic salts were filtered off and the filtrate was evaporated to a solid. The solid was recrystallized from 1:1 dichloromethane/pentane to yield 2.14 g of solid, mp 163° C.

ANALYSIS: Calculated for $C_{20}H_{19}ClN_2O$: 70.90% C, 5.65% H, 8.27% N. Found: 70.75% C, 5.78% H, 8.21% N.

EXAMPLE 68
9-Benzylamino-6-trifluoromethyl-1,2,3,4-tetrahydroacridin-1-ol

To a cooled solution of 3.5 g of 9-benzylamino-3,4-dihydro-6-trifluoromethylacridin-1(2H)-one in 60 ml of tetrahydrofuran was added 5 ml of 1M solution of lithium aluminum hydride in tetrahydrofuran. This was stirred for 1 hour at ice temperature.

The reaction was then quenched with 5 ml of saturated ammonium chloride solution. The inorganics were filtered and rinsed with ethyl acetate, and the combined organics were dried over anhydrous magnesium sulfate. This was concentrated to a solid, mp 153°–157° C., which was recrystallized from isopropyl ether to yield 2.0 g of an analytically pure powder, mp 156°–158° C.

ANALYSIS: Calculated for $C_{21}H_{19}F_3N_2O$: 67.73% C, 5.14% H, 7.52% N. Found: 67.49% C, 5.01% H, 7.42% N.

EXAMPLE 69
9-(2-Methylbenzylamino)-1,2,3,4-tetrahydroacridin-1-ol 3,4-Dihydro-9-(2-methylbenzylamino)acridin-1(2H)-one (4.15 g) was suspended in 100 ml of THF and chilled with ice-water. 1M lithium aluminum hydride in THF (8.0 ml) was added dropwise through a syringe and then the reaction mixture was stirred 30 minutes in the cold. It was quenched by the sequential addition of 0.5 ml of water, 0.5 ml of 15% sodium hydroxide and 1.5 ml of water. The inorganic salts were filtered and the organic phase was evaporated to obtain an amorphous solid product. Recrystallization from ethyl acetate gave 3.38 g, mp 167°–169° C.

ANALYSIS: Calculated for $C_{21}H_{22}N_2O$: 79.21% C, 6.97% H, 8.80% N. Found: 79.18% C, 7.10% H, 8.78% N.

EXAMPLE 70

9-(3-Methylbenzylamino)-1,2,3,4-tetrahydroacridin-1-ol 3,4-Dihydro-9-(3-methylbenzylamino)acridin-1(2H)-one (3.70 g) was dissolved in 100 ml of dry THF and chilled in ice-water. 1M lithium aluminum hydride in THF (7.0 ml) was added and the reaction stirred 30 minutes in the cold. The reaction mixture was quenched by the sequential addition of 0.5 ml of water, 0.5 ml of 15% sodium hydroxide and 1.5 ml of water. The inorganic salts were filtered from the reaction mixture and the organic phase was evaporated to an oil. Trituration with ether gave a solid that was recrystallized from ethyl acetate/pentane to obtain 3.22 g, mp 133°–134° C.

ANALYSIS: Calculated for $C_{21}H_{22}N_2O$: 79.21% C, 6.97% H, 8.80% N. Found: 79.12% C, 7.05% H, 8.54% N.

EXAMPLE 71

9-(4-Methylbenzylamino)-1,2,3,4-tetrahydroacridin-1-ol 3,4-Dihydro-9-(4-methylbenzylamino)acridin-1(2H)-one (5.71 g) was dissolved in 100 ml of dry THF, chilled with ice-water, and then 9.0 ml of 1M lithium aluminum hydride in THF was added. After 15 minutes the reaction was quenched by the sequential addition of 0.4 ml of water, 0.4 ml of 15% sodium hydroxide, and 1.2 ml of water. The inorganic salts were filtered off and washed with warm THF and then the combined organic phase was evaporated and the residue recrystallized from dichloromethane-pentane to obtain 4.77 g of analytically pure product, mp 176°–178° C.

ANALYSIS: Calculated for $C_{21}H_{22}N_2O$: 79.21% C, 6.97% H, 8.80% N. Found: 79.19% C, 6.97% H, 8.75% N.

EXAMPLE 72

9-(2-Methoxybenzylamino)-1,2,3,4-tetrahydroacridin-1-ol 3,4-Dihydro-9-(2-methoxybenzylamino)acridin-1(2H)-one (4.0 g) was dissolved in 100 of dry THF and chilled in ice-water. 1M lithium aluminum hydride in THF (6.5 ml) was added through a syringe. The reaction mixture was stirred 30 minutes in the cold and then an additional 2.0 ml of 1M lithium aluminum hydride solution was added. The reaction mixture was quenched by the sequential addition of 0.5 ml of water, 0.5 ml of 15% sodium hydroxide and 1.5 ml of water. The inorganic salts were filtered from the reaction and the organic phase was evaporated to a gum. Trituration with ether gave a solid (2.95 g). Analytically pure material was obtained by recrystallization from ethyl acetate-pentane, mp 115°–117° C.

ANALYSIS: Calculatated for $C_{21}H_{22}N_2O_2$: 75.42% C, 6.63% H, 8.38% N. Found: 75.38% C, 6.82% H, 8.31% N.

EXAMPLE 73

9-(3-Methoxybenzylamino)-1,2,3,4-tetrahydroacridin-1-ol 3,4-Dihydro-9-(3-methoxybenzylamino)acridin-1(2H)-one (4.0 g) was dissolved in 75 ml of dry THF, the solution was chilled with ice-water, and 1M lithium aluminum hydride (6.5 ml) was added dropwise through a syringe. After 30 minutes TLC showed that the reaction was complete, so the reaction was quenched by the successive addition of 0.4 ml of water, 0.4 ml of 15% sodium hydroxide, and 1.2 ml of water. The inorganic salts were filtered off and the organic phase was evaporated to an oil. Trituration with ether gave a solid that was filtered off and then recrystallized from ether-pentane to give 2.2 g of analytically pure product, mp 123°–125° C.

ANALYSIS: Calculated for $C_{21}H_{22}N_2O_2$: 75.42% C, 6.63% H, 8.38% N. Found: 75.59% C, 6.80% H, 8.34% N.

EXAMPLE 74

9-(4-Methoxybenzylamino)-1,2,3,4-tetrahydroacridin-1-ol 3,4-Dihydro-9-(4-methoxybenzylamino)acridin-1(2H)-one (4.25 g) was dissolved in 75 ml of dry THF and chilled with ice-water. 1M lithium aluminum hydride in THF (7.0 ml) was then added dropwise. After 15 minutes the reaction was quenched by the sequential dropwise addition of 0.4 ml of water, 0.4 ml of 15% sodium hydride and 1.2 ml of water. The inorganic salts were filtered off, the solvents were evaporated, and the residue recrystallized from dichloromethane-ether to give 3.0 g of analytically pure product, mp 163°–165° C.

ANALYSIS: Calculated for $C_{21}H_{22}N_2O_2$: 75.42% C, 6.63% H, 8.38% N. Found: 75.01% C, 6.89% H, 8.32% N.

EXAMPLE 75

9-(3-Fluorobenzylamino)-1,2,3,4-tetrahydroacridin-1-ol

In 100 ml of THF was dissolved 3.00 g of 3,4-dihydro-9-(3-fluorobenzylamino)acridin-1(2H)-one. The mechanically stirred solution was cooled in ice under nitrogen and 4.68 ml of 1M lithium aluminum hydride in THF was added dropwise over 15 minutes. After 0.5 hour, analysis by TLC indicated the reaction was complete, so it was neutralized with 1 ml of saturated ammonium chloride solution and the resulting salts were filtered. The filtrate was evaporated to an oil which crystallized on trituration with pentane. The solid was filtered and recrystallized from 1:1 dichloromethane/pentane to yield 2.50 g of solid, mp 128° C.

ANALYSIS: Calculated for $C_{20}H_{19}FN_2O$: 74.51% C, 5.94% H, 8.69% N. Found: 74.78% C, 5.94% H, 8.93% N.

EXAMPLE 76

9-(4-fluorobenzylamino)-1,2,3,4-tetrahydroacridin-1-ol

In 100 ml of dry THF was dissolved 3.00 g of 3,4-dihydro-9-(4-fluorobenzyl)aminoacridin-1(2H)-one. The mechanically stirred solution was cooled in ice and 4.68 ml of 1M LiAlH$_4$ in THF was added over 5 minutes. After ½ hour the reaction was complete by TLC. The excess hydride was neutralized with 1 ml of saturated ammonium chloride solution and the resulting salts were filtered. The THF filtrate was evaporated to a solid which was recrystallized from 1:1 dichloromethane/pentane to yield 2.47 g of solid, mp 169.5°–170° C.

ANALYSIS: Calculated for $C_{20}H_{19}FN_2O$: 74.51% C, 5.94% H, 8.69% N. Found: 74.42% C, 5.86% H, 8.83% N.

EXAMPLE 77

6-Chloro-9-(4-fluorobenzylamino)-1,2,3,4,-tetrahydroacridin-1-ol

In 100 ml of dry THF was added 4.06 g of 6-chloro-3,4-dihydro-9-(4-fluorobenzylamino)acridin-1(2H)-one and the mechanically stirred solution was cooled to 10° C. under a nitrogen atmosphere. To the reaction was added 5.8 ml of 1M LiAlH$_4$ in THF over 15 minutes. After ½ hour the reaction was complete by TLC analysis, so it was quenched with 1 ml of saturated ammonium chloride solution and the inorganic salts were filtered off. The filtrate was evaporated to a solid which was recrystallized from dichloromethane to yield 3.18 g of solid. The compound went through a crystal structure change at 176°–177° C. before melting at 187°–188° C.

ANALYSIS: Calculated for $C_{20}H_{18}ClFN_2O$: 67.32% C, 5.08% H, 7.85% N. Found: 67.03% C, 4.96% H, 7.60% N.

EXAMPLE 78

9-(2-Chlorobenzylamino)-1,2,3,4-tetrahydroacridin-1-ol

To a cooled suspension of 9-(2-chlorobenzylamino)-3,4-dihydroacridin-1(2H)-one (4.0 g) in 75 ml of tetrahydrofuran was added 6.5 ml of 1M solution of lithium aluminum hydride in THF. This was stirred at ice bath temperature for 1.5 hours.

The reaction was then quenched with 15 ml of saturated ammonium chloride solution. The salts were filtered, washed with ethyl acetate and the filtrate was dried over anhydrous magnesium sulfate. This was concentrated to a solid which was triturated with ethyl ether and filtered to give 3.8 g of a powder, mp 136°–141° C. This was recrystallized from ethyl acetate to give 2.75 g of an analytically pure solid, mp 141°–143° C.

ANALYSIS: Calculated for $C_{20}H_{19}ClN_2O$: 70.89% C, 5.65% H, 8.27% N. Found: 70.80% C, 5.55% H, 8.19% N.

EXAMPLE 79

9-(3-Chlorobenzylamino)-1,2,3,4-tetrahydroacridin-1-ol

To a ice cooled suspension of 9-(3-chlorobenzylamino)-3,4-dihydroacridin-1(2H)-one (3.6 g) in 75 ml of tetrahydrofuran was added a 1M solution of lithium aluminum hydride in THF (6 ml). This was stirred at ice bath temperature for 45 minutes.

The reaction was then quenched with 15 ml of saturated ammonium chloride solution, the precipitates were filtered and washed with ethyl acetate and the organics were dried over anhydrous magnesium sulfate. This was concentrated to a solid which was triturated with ethyl ether to give 3.6 g of a solid, mp 140°–142° C.

ANALYSIS: Calculated for $C_{20}H_{19}ClN_2O$: 70.89% C, 5.65% H, 8.27% N. Found: 71.01% C, 5.85% H, 8.26% N.

EXAMPLE 80

9-(4-Chlorobenzylamino)-1,2,3,4-tetrahydroacridin-1-ol

To a cooled solution of 6.25 g of 9-(4-chlorobenzylamino)-3,4-dihydroacridin-1(2H)-one in 140 ml of tetrahydrofuran was added 10 ml of 1M LiAlH$_4$ solution in THF. This was stirred at ice bath temperature for 1 hour.

The reaction was then quenched with 10 ml of saturated ammonium chloride solution, the inorganics were filtered and washed with ethyl acetate. The combined organics were dried over anhydrous magnesium sulfate and concentrated to a solid. This was recrystallized from ethyl acetate to yield 5.1 g of an analytically pure solid, mp 175.5°–177.5° C.

ANALYSIS: Calculated for $C_{20}H_{19}ClN_2O$: 70.89% C, 5.65% H, 8.27% N. Found: 71.09% C, 5.69% H, 8.24% N.

EXAMPLE 81

1,2,3,4-Tetrahydro-9-(2-trifluoromethylbenzylamino)acridin-1-ol

In 100 ml of dry THF was dissolved 4.31 g of 3,4-dihydro-9-(2-trifluoromethylbenzylamino)acridin-1(2H)-one and the mechanically stirred solution was cooled to 10° C. under nitrogen. To it was added 5.8 ml of 1M LiAlH$_4$ in THF dropwise over 15 minutes. Within 0.5 hour of addition the reaction was complete by TLC, so it was quenched with 1 ml of saturated ammonium chloride and the salts were filtered. The filtrate was evaporated to a solid which was dissolved in dichloromethane. The dichloromethane solution was dried over anhydrous magnesium sulfate and filtered. The filtrate was refluxed and pentane was added to effect crystallization. The crystals were collected from the cooled mother liquor to yield 3.44 g of solid, mp 158°–160° C.

ANALYSIS: Calculated for $C_{21}H_{19}F_3N_2O$: 67.73% C, 5.14% H, 7.52% N. Found: 67.88% C, 5.26% H, 7.58% N.

EXAMPLE 82

6-Fluoro-1,2,3,4-tetrahydro-9-(2-trifluoromethylbenzylamino)-acridin-1-ol

To a cooled solution of 5.7 g of 3,4-dihydro-6-fluoro-9-(2-trifluoromethylbenzylamino)acridin-1(2H)-one in 80 ml of tetrahydrofuran was added 7.5 ml of 1 molar solution of lithium aluminium hydride in THF. This was stirred for 0.5 hour and then quenched with 6 ml of saturated ammonium chloride solution. The inorganics were filtered, rinsed with ethyl acetate and the combined organics were dried over anhydrous magnesium sulfate. This was concentrated to a solid which was triturated with ether to give 5.1 g of a powder. This was twice recrystallized from ethyl acetate/hexane to give 3.1 g of analytically pure crystals, mp 149°–153° C.

ANALYSIS: Calculated for $C_{21}H_{18}F_4N_2O$: 64.61% C, 4.65% H, 7.18% N. Found: 64.76% C, 4.75% H, 7.06% N.

EXAMPLE 83

1,2,3,4,-Tetrahydro-9-(3-trifluoromethylbenzylamino)acridin-1-ol

In 100 ml dry THF was dissolved in 3.86 g of 3,4-dihydro-9-(3-trifluoromethylbenzyl)aminoacridin-1(2H)-one. The solution was stirred mechanically under nitrogen and cooled in ice. To it was added 5.2 ml of 1M LiAlH$_4$ in THF dropwise. After stirring an additional 0.5 hour, the reaction was complete. It was neutralized with 1 ml of saturated ammonium chloride and the salts were filtered off. The THF filtrate was evaporated to an oil which solidified upon trituration with pentane. The solid was recrystallized from 1:1 dichloromethane/pentane to yield 3.12 g of solid, mp 154°–155° C.

ANALYSIS: Calculated for $C_{21}H_{19}F_3N_2O$: 67.73% C, 5.14% H, 7.52% N. Found: 67.92% C, 5.19% H, 7.65% N.

EXAMPLE 84

1,2,3,4-Tetrahydro-9-(4-trifluoromethylbenzylamino)acridin-1-ol

In 100 ml of dry THF was dissolved 2.49 g of 3,4-dihydro-9-(4-trifluoromethylbenzylamino)acridin-1(2H)-one. The mechanically stirred solution was cooled under nitrogen to 10° C. and 3.4 ml of 1M LiAlH$_4$ in THF was added dropwise over 10 minutes. After ½ hour of stirring, the reaction was complete. It was neutralized with 1 ml of saturated ammonium chloride solution and the resulting salts were filtered. The filtrate was evaporated to a solid which was recrystallized from 1:1 dichloromethane/pentane to yield 1.91 g of solid, mp 174°–176° C.

ANALYSIS: Calculated for $C_{21}H_{19}F_3N_2O$: 67.73% C, 5.14% H, 7.52% N. Found: 68.11% C, 5.02% H, 7.47% N.

EXAMPLE 85

9-[(2,3,4,5,6-Pentafluorobenzyl)amino]-1,2,3,4-tetrahydroacridin-1-ol, fumarate

To a cooled solution of 3.8 g of 3,4-dihydro-9-[(2,3,4,5,6-pentafluorobenzyl)amino]acridin-1(2h)-one in 60 ml of tetrahydrofuran was added 5 of 1M solution of lithium aluminum hydride in tetrahydrofuran. After 1 hour, an additional 1 ml of the LiAlH$_4$ solution was added. This was stirred for 0.5 hour and then quenched with 5 ml of saturated ammonium chloride solution. The inorganics were filtered and rinsed with warm THF. The filtrate was diluted with ethyl acetate and dried over anhydrous magnesium sulfate. This was then concentrated to a solid which was triturated with diethyl ether to give 2.25 g of a powder, mp 202°–207° C. decomp.

The free base was dissolved in 150 ml of ethanol and 50 ml of methanol and acidified with an ethanolic fumaric acid solution. The resulting crystals were collected and dried to give 2.15 g of a solid, mp 214°–216° C. decomp.

ANALYSIS: Calculated for $C_{20}H_{15}F_5N_2O$: 56.47% C, 3.75% H, 5.49% N. Found: 56.56% C, 3.96% H, 5.47% N.

EXAMPLE 86

9-(4,4-Diphenylbutyl)amino-1,2,3,4-tetrahydroacridin-1-ol

In 30 ml of dry THF was dissolved 3.00 g of 3,4-dihydro-9-(4,4-diphenylbutyl)aminoacridin-1(2H)-one and the mechanically stirred solution was cooled in an ice bath under nitrogen atmosphere. To the solution under nitrogen was added 6.48 ml of 1M LiAlH$_4$ in THF. Within 0.5 hour after addition the reaction was complete by TLC. The reaction was neutralized with 1 ml of saturated ammonium chloride solution and the inorganics were filtered off. The filtrate was evaporated to an oil and the oil was triturated with 30 ml of 10:1 ether/acetone to yield 2.22 g of solid, mp 147°–148° C. This sample was combined with a 1.0 g sample of an identical previous run and recrystallized from acetone to yield 2.87 g of powder, mp 146°–148° C.

ANALYSIS: Calculated for $C_{29}H_{30}N_2O$: 82.43% C, 7.16% H, 6.63% N. Found: 82.77% C, 7.51% H, 6.68% N.

EXAMPLE 87

9-[4,4-Bis(3-fluorophenyl)butylamino]-1,2,3,4-tetrahydroacridin-1-ol, hemi-fumarate To a cooled solution of 5.3 g of 9-[4,4-bis(3-fluorophenyl)butylamino]-3,4-dihydroacridin-1(2H)-one in 100 ml of tetrahydrofuran was added 7 ml of 1M solution of lithium aluminium hydride in THF. This was stirred for 2 hours and then quenched with 5 ml of saturated ammonium chloride solution. This was then diluted with ethyl acetate, filtered and the inorganics were rinsed with ethyl acetate. The combined organics were then dried over anhydrous magnesium sulfate and passed through a column of magnesium silicate (ethyl acetate). This gave a fibrous semi-solid which was dissolved in ethanol, acidified with an ethanolic solution of fumaric acid and diluted with ethyl ether. The resulting crystals were collected and dried to give 2.35 g of a solid, mp 180°–181° C. decomp.

ANALYSIS: Calculated for $C_{29}H_{28}F_2N_2O \cdot 0.5C_4H_4O_4$: 72.07% C, 5.85% H, 5.42% N. Found: 72.20% C, 5.83% H, 5.41% N.

EXAMPLE 88

9-[4,4-Bis(4-fluorophenyl)butylamino]-1,2,3,4-tetrahydroacridin-1-ol

To a cooled solution of 4.2 g of 3,4-dihydro-9-[4,4-bis(4-fluorophenyl)butylamino]acridin-1(2H)-one in tetrahyddrofuran was added 5 ml of 1M solution of lithium aluminum hydride in tetrahydrofuran. This was stirred for 0.5 hour at ice bath temperature.

The reaction was then quenched with 5 ml of saturated ammonium chloride solution, the inorganics were filtered and rinsed with ethyl acetate and the combined organics were dried over anydrous magnesium sulfate. This was concentrated to a solid which was triturated with ethyl ether to give 3.4 g of a solid, mp 155°–158° C. This was recrystallized from isopropyl ether/methanol (15:1) to yield 2.15 g of an analytically pure solid, mp 157°–159° C.

ANALYSIS: Calculated for $C_{29}H_{28}F_2N_2O$: 75.96% C, 6.15% H, 6.11% N. Found: 75.81% C, 6.12% H, 6.07% N.

EXAMPLE 89

9-(3-Phenoxypropylamino)-1,2,3,4-tetrahydroacridin-1-ol

In 100 ml of dry THF was dissolved 2.47 g of 3,4-dihydro-9-(3-phenoxypropyl)aminoacridin-1(2H)-one. The mechanically stirred solution was cooled in ice under nitrogen and 3.6 ml of 1M LiAlH$_4$ in THF was added dropwise over 5 minutes. After 0.5 hour the reaction was complete by TLC. The reaction was neutralized with 1 ml of saturated ammonium chloride solution and the inorganic salts were filtered off. The filtrate was evaporated to an oil which solidified when triturated with pentane. The solid was recrystallized from 1:1 dichloromethane/pentane to yield after drying 2.17 g of product, mp 138°–140° C.

ANALYSIS: Calculated for $C_{22}H_{24}N_2O_2$: 75.83% C, 6.94% H, 8.04% N. Found: 75.22% C, 7.17% H, 7.94% N.

EXAMPLE 90

9-[[2-[Bis(4-fluorophenyl)methoxy]ethyl]amino]-1,2,3,4-tetrahydroacridin-1-ol To a cooled solution of 5.55 g of 3,4-dihydro-9-[[2-[bis(4-fluorophenyl)methoxy]ethyl]amino]acridin-1(2H)-one in 100 ml of tetrahydrofuran was added 6.5 ml of 1M solution of lithium aluminum hydride in tetrahydrofuran. This was stirred for 1 hour at ice bath temperature.

The reaction was then quenched with 5 ml of saturated ammonium chloride solution, and the inorganics were filtered and washed with ethyl acetate. The combined organics were then dried over anhydrous magnesium sulfate. This was concentrated to a solid which was triturated with diethyl ether to give 3.45 g of a solid, mp 180°–183° C.

ANALYSIS: Calculated for $C_{28}H_{26}F_2N_2O_2$: 73.02% C, 5.69% H, 6.08% N. Found: 73.31% C, 5.78% H, 6.10% N.

EXAMPLE 91

9-[4-(Benzyloxy)benzylamino]-1,2,3,4-tetrahydroacridin-1-ol

To a cooled suspension of 4.75 g of 3,4-dihdyro-9-[4-(benzyloxy)benzylamino]acridin-1(2H)-one in 75 ml of tetrahydrofuran was added 6 ml of 1M solution of lithium aluminum hydride in tetrahydofuran. This was stirred for 1 hour.

The reaction was then quenched with 5 ml of saturated ammonium chloride solution and the inorganics were filtered and rinsed with ethyl acetate. This was dried over anhydrous magnesium sulfate and concentrated to a solid which was triturated with ethyl ether and recrystallized from acetone to give 1.65 g of an analytically pure powder, mp 172°–175° C.

ANALYSIS: Calculated for $C_{27}H_{26}N_2O_2$: 79.00% C, 6.39% H, 6.82% N. Found: 78.83% C, 6.43% H, 6.67% N.

EXAMPLE 92

9-[(2-Thienyl)methylamino]-1,2,3,4-tetrahydroacridin-1-ol, fumarate

To a cooled solution of 4.0 g of 3,4-dihydro-9-[(2-thienyl)methylamino]acridin-1(2H)-one in 75 ml of tetrahydrofuran was added 7 ml of 1M solution of lithium aluminum hydride in tetrahydrofuran. This was stirred for 1 hour.

The reaction was then quenched with 5 ml of saturated ammonium chloride solution, and the inorganics were filtered and rinsed with ethyl acetate. The organics were then dried over anhydrous magnesium sulfate and concentrated to a solid which was triturated with ethyl ether to give 3.3 g of a solid, mp 149°–154° C. This solid was recrystallized from ethyl acetate and the resulting solid was dissolved in a mixture of 100 ml isopropanol and 25 ml of methanol and the solution was acidified with a isopropanolic solution of fumaric acid. The resulting solid was filtered and dried to give 2.6 g of an analytically pure solid, mp 183°–184° C. decomp.

ANALYSIS: Calculated for $C_{18}H_{18}N_2OS \cdot C_4H_4O_4$: 61.95% C, 5.20% H, 6.57% N. Found: 61.52% C, 5.44% H, 6.24% N.

EXAMPLE 93

9-Amino-1,2,3,4-tetrahydro-cyclopenta[b]quinolin-1-ol, maleate

To a cooled suspension of 3.2 g of 9-amino-2,3-dihydrocyclopenta[b]quinolin-1-one in 100 ml of tetrahydrofuran was added 17 ml of 1M solution of lithium aluminum hydride in THF. This was stirred for 2 hours and thereafter quenched with 12 ml of saturated ammonium chloride solution. This was diluted with ethyl acetate and filtered. This solution was allowed to stand overnight during which time crystals were formed. These were filtered and the filtrate was concentrated to a solid which was triturated with isopropanol/ethyl ether to give overall 1.9 g of a solid, mp 195°–205° C. decomp. This was suspended in 100 ml of isopropanol and 1.27 g of maleic acid. From this, a solution resulted which was filtered and diluted with 50 ml of ethyl ether. The resulting crystals were filtered and recrystallized from tetrahydrofuran/methanol/ethyl ether (4:1:4) to give 1.5 g of an analytically pure solid, mp 160°–162° C. d.

ANALYSIS: Calculated for $C_{12}H_{12}N_2O \cdot C_4H_4O_4$: 60.75% C, 5.10% H, 8.86% N. Found: 60.35% C, 5.18% H, 8.69% N.

We claim:

1. A compound having the formula

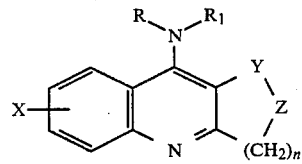

wherein n is 1, 2 or 3; X is hydrogen, loweralkyl, loweralkoxy, halogen, hydroxy, nitro, trifluoromethyl, NHCOR$_2$ where R$_2$ is loweralkyl, or NR$_3$R$_4$ where R$_3$ and R$_4$ are independently hydrogen or loweralkyl; R is hydrogen or loweralkyl; R$_1$ is hydrogen, loweralkyl, diloweralkylaminoloweralkyl, arylloweralkyl, diarylloweralkyl, furylloweralkyl, thienylloweralkyl, oxygen-bridged arylloweralkyl, oxygen-bridged diarylloweralkyl, oxygen-bridged furylloweralkyl, oxygen-bridged thienylloweralkyl; Y is C=O or CR$_5$OH where R$_5$ is hydrogen or loweralkyl; Z is CH$_2$ or C=CR$_6$R$_7$ where R$_6$ and R$_7$ are independently hydrogen or loweralkyl; an optical antipode thereof, or a pharmaceutically acceptable acid addition salt thereof.

2. The compound as defined in claim 1, where n is 2.
3. The compound as defined in claim 2, where R is H.
4. The compound as defined in claim 3, where Y is C=O.
5. The compound as defined in claim 4, where Z is CH$_2$.
6. The compound as defined in claim 4, where Z is C=CR$_6$R$_7$.
7. The compound as defined in claim 6, where Z is C=CH$_2$.
8. The compound as defined in claim 3, where Y is CR$_5$OH.
9. The compound as defined in claim 8, where Y is CHOH.
10. The compound as defined in claim 8, where Z is CH$_2$.
11. The compound as defined in claim 9, where Z is C=CR$_6$R$_7$.

12. The compound as defined in claim 11, where Z is C=CH₂.

13. The compound as defined in claim 1, where n is 1.

14. The compound as defined in claim 13, where R is H.

15. The compound as defined in claim 14, where Y is C=O and Z is CH₂.

16. The compound as defined in claim 14, where Y is CHOH and Z is CH₂.

17. The compound as defined in claim 1, which is 9-amino-3,4-dihydro-6-methylacridin-1(2H)-one.

18. The compound as defined in claim 1, which is 9-amino-3,4-dihydro-6-methoxyacridin-1(2H)-one.

19. The compound as defined in claim 1, which is 9-amino-3,4-dihydro-6-fluoroacridin-1(2H)-one.

20. The compound as defined in claim 1, which is 9-amino-3,4-dihydro-6-trifluoromethylacridin-1(2H)-one.

21. The compound as defined in claim 1, which is 3,4-dihydro-9-[2-(dimethylamino)ethyl]aminoacridin-1(2H)-one.

22. The compound as defined in claim 1, which is 9-benzylamino-3,4-dihydro-6-methylacridin-1(2H)-one.

23. The compound as defined in claim 1, which is 9-benzylamino-3,4-dihydro-6-fluoroacridin-1(2H)-one.

24. The compound as defined in claim 1, which is 9-benzylamino-6-chloro-3,4-dihydroacridin-1(2H)-one.

25. The compound as defined in claim 1, which is 9-benzylamino-3,4-dihydro-6-trifluoromethylacridin-1(2H)-one.

26. The compound as defined in claim 1, which is 3,4-dihydro-9-(2-methylbenzylamino)acridin-1(2H)-one.

27. The compound as defined in claim 1, which is 3,4-dihydro-9-(3-methylbenzylamino)acridin-1(2H)-one.

28. The compound as defined in claim 1, which is 3,4-dihydro-9-(4-methylbenzylamino)acridin-1(2H)-one.

29. The compound as defined in claim 1, which is 3,4-dihydro-9-(2-methoxybenzylamino)acridin-1(2H)-one.

30. The compound as defined in claim 1, which is 3,4-dihydro-9-(3-methoxybenzylamino)acridin-1(2H)-one.

31. The compound as defined in claim 1, which is 3,4-dihydro-9-(4-methoxybenzylamino)acridin-1(2H)-one.

32. The compound as defined in claim 1, which is 3,4-dihydro-9-(3-fluorobenzylamino)acridin-1(2H)-one.

33. The compound as defined in claim 1, which is 3,4-dihydro-9-(4-fluorobenzylamino)acridin-1(2H)-one.

34. The compound as defined in claim 1, which is 6-chloro-3,4-dihydro-9-(4-fluorobenzylamino)acridin-1(2H)-one.

35. The compound as defined in claim 1, which is 9-(2-chlorobenzylamino)-3,4-dihydroacridin-1(2H)-one.

36. The compound as defined in claim 1, which is 9-(3-chlorobenzylamino)-3,4-dihydroacridin-1(2H)-one.

37. The compound as defined in claim 1, which is 9-(4-chlorobenzylamino)-3,4-dihydroacridin-1(2H)-one.

38. The compound as defined in claim 1, which is 3,4-dihydro-9-[(2,3,4,5,6-pentafluorobenzyl)amino]acridin-1(2H)-one.

39. The compound as defined in claim 1, which is 3,4-dihydro-9-(2-trifluoromethylbenzylamino)acridin-1(2H)-one.

40. The compound as defined in claim 1, which is 3,4-dihydro-6-fluoro-9-(2-trifluoromethylbenzylamino)acridin-1(2H)-one.

41. The compound as defined in claim 1, which is 3,4-dihydro-9-(3-trifluoromethylbenzylamino)acridin-1(2H)-one.

42. The compound as defined in claim 1, which is 3,4-dihydro-9-(4-trifluoromethylbenzylamino)acridin-1(2H)-one.

43. The compound as defined in claim 1, which is 3,4-dihydro-9-(4,4-diphenylbutylamino)-6-trifluoromethylacridin-1(2H)-one.

44. The compound as defined in claim 1, which is 9-[4,4-bis(3-fluorophenyl)butylamino]-3,4-dihydroacridin-1(2H)-one.

45. The compound as defined in claim 1, which is 3,4-dihydro-9-[4,4-bis(4-fluorophenyl)butylamino]acridin-1(2H)-one.

46. The compound as defined in claim 1, which is 3,4-dihydro-9-(3-phenoxypropylamino)acridin-1(2H)-one.

47. The compound as defined in claim 1, which is 9-[2-[bis(4-fluorophenyl)methoxy]ethylamino]-3,4-dihydroacridin-1(2H)-one.

48. The compound as defined in claim 1, which is 9-[4-(benzyloxy)benzylamino]-3,4-dihydroacridin-1(2H)-one.

49. The compound as defined in claim 1, which is 3,4-dihydro-9-[(2-thienyl)methylamino]acridin-1(2H)-one.

50. The compound as defined in claim 1, which is 9-amino-2,3-dihydro-cyclopenta[b]quinolin-1-one.

51. The compound as defined in claim 1, which is 9-amino-6-methoxy-1,2,3,4-tetrahydroacridin-1-ol.

52. The compound as defined in claim 1, which is 9-amino-6-fluoro-1,2,3,4-tetrahydroacridin-1-ol.

53. The compound as defined in claim 1, which is 9-amino-1,2,3,4-tetrahydro-6-trifluoromethylacridin-1-ol.

54. The compound as defined in claim 1, which is 9-[2-(dimethylamino)ethyl]amino-1,2,3,4-tetrahydroacridin-1-ol.

55. The compound as defined in claim 1, which is 9-benzylamino-6-methyl-1,2,3,4-tetrahydroacridin-1-ol.

56. The compound as defined in claim 1, which is 9-benzylamino-6-fluoro-1,2,3,4-tetrahydroacridin-1-ol.

57. The compound as defined in claim 1, which is 9-benzylamino-6-chloro-1,2,3,4-tetrahydroacridin-1-ol.

58. The compound as defined in claim 1, which is 9-benzylamino-1,2,3,4-tetrahydro-6-trifluoromethylacridin-1-ol.

59. The compound as defined in claim 1, which is 9-(2-methylbenzylamino)-1,2,3,4-tetrahydroacridin-1-ol.

60. The compound as defined in claim 1, which is 9-(3-methylbenzylamino)-1,2,3,4-tetrahydroacridin-1-ol.

61. The compound as defined in claim 1, which is 9-(4-methylbenzylamino)-1,2,3,4-tetrahydroacridin-1-ol.

62. The compound as defined in claim 1, which is 9-(2-methoxybenzylamino)-1,2,3,4-tetrahydroacridin-1-ol.

63. The compound as defined in claim 1, which is 9-(3-methoxybenzylamino)-1,2,3,4-tetrahydroacridin-1-ol.

64. The compound as defined in claim 1, which is 9-(4-methoxybenzylamino)-1,2,3,4-tetrahydroacridin-1-ol.

65. The compound as defined in claim 1, which is 9-(3-fluorobenzyl)amino-1,2,3,4-tetrahydroacridin-1-ol.

66. The compound as defined in claim 1, which is 9-(4-fluorobenzyl)amino-1,2,3,4-tetrahydroacridin-1-ol.

67. The compound as defined in claim 1, which is 6-chloro-9-(4-fluorobenzylamino)-1,2,3,4-tetrahydroacridin-1-ol.

68. The compound as defined in claim 1, which is 9-(2-chlorobenzylamino)-1,2,3,4-tetrahydroacridin-1-ol.

69. The compound as defined in claim 1, which is 9-(3-chlorobenzylamino)-1,2,3,4-tetrahydroacridin-1-ol.

70. The compound as defined in claim 1, which is 9-(4-chlorobenzylamino)-1,2,3,4-tetrahydroacridin-1-ol.

71. The compound as defined in claim 1, which is 1,2,3,4-tetrahydro-9-(2-trifluoromethylbenzyl)aminoacridin-1-ol.

72. The compound as defined in claim 1, which is 6-fluoro-1,2,3,4-tetrahydro-9-(2-trifluoromethylbenzylamino)acridin-1-ol.

73. The compound as defined in claim 1, which is 1,2,3,4-tetrahydro-9-(3-trifluoromethylbenzylamino)acridin-1-ol.

74. The compound as defined in claim 1, which is 1,2,3,4-tetrahydro-9-(4-trifluoromethylbenzylamino)acridin-1-ol.

75. The compound as defined in claim 1, which is 9-[(2,3,4,5,6-pentafluorobenzyl)amino]-1,2,3,4-tetrahydroacridin-1-ol.

76. The compound as defined in claim 1, which is 9-(4,4-diphenylbutyl)amino-1,2,3,4-tetrahydroacridin-1-ol.

77. The compound as defined in claim 1, which is 9-[4,4-bis(3-fluorophenyl)butylamino]-1,2,3,4-tetrahydroacridin-1-ol.

78. The compound as defined in claim 1, which is 9-[4,4-bis(4-fluorophenyl)butylamino]-1,2,3,4-tetrahydroacridin-1-ol.

79. The compound as defined in claim 1, which is 9-(3-phenoxypropylamino)-1,2,3,4-tetrahydroacridin-1-ol.

80. The compound as defined in claim 1, which is 9-[[2-[bis(4-fluorophenyl)methoxy]ethyl]amino]-1,2,3,4-tetrahydroacridin-1-ol.

81. The compound as defined in claim 1, which is 9-[4-(benzyloxy)benzylamino]-1,2,3,4-tetrahydroacridin-1-ol.

82. The compound as defined in claim 1, which is 9-[(2-thienyl)methylamino]-1,2,3,4-tetrahydroacridin-1-ol.

83. The compound as defined in claim 1, which is 9-amino-1,2,3,4-tetrahydro-cyclopenta[b]quinolin-1-ol.

84. A pharmaceutical composition which comprises an effective memory enhancing amount of a compound defined in claim 1.

85. A pharmaceutical composition which comprises an effective memory enhancing amount of a compound defined in claim 2.

86. A pharmaceutical composition which comprises an effective memory enhancing amount of a compound defined in claim 13.

87. A method of treating a patient in need of memory enhancement, wherein an effective memory enhancing amount of a compound defined in claim 1 is administered to the patient.

88. A method of treating a patient in need of memory enhancement, wherein an effective memory enhancing amount of a compound defined in claim 2 is administered to the patient.

89. A method of treating a patient in need of memory enhancement, wherein an effective memory enhancing amount of a compound defined in claim 13 is administered to the patient.

* * * * *

UNITED STATES PATENT AND TRADEMARK OFFICE
CERTIFICATE OF CORRECTION

PATENT NO. : 4,695,573

DATED : September 22, 1987

INVENTOR(S) : Gregory M. Shutske and Frank A. Pierrat

It is certified that error appears in the above-identified patent and that said Letters Patent is hereby corrected as shown below: On the title page In the "Notice" section:

"Mar. 6, 2001" should read --December 23, 2003 --

Signed and Sealed this

Seventh Day of June, 1988

Attest:

DONALD J. QUIGG

Attesting Officer

Commissioner of Patents and Trademarks